US012810388B2

(12) United States Patent
Yang et al.

(10) Patent No.: US 12,810,388 B2
(45) Date of Patent: Nov. 24, 2026

(54) SYSTEMS AND METHODS FOR ULTRASOUND IMAGE PROCESSING

(71) Applicant: WUHAN UNITED IMAGING HEALTHCARE CO., LTD., Wuhan (CN)

(72) Inventors: Zuowei Yang, Wuhan (CN); Tong Li, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 512 days.

(21) Appl. No.: 18/462,422

(22) Filed: Sep. 7, 2023

(65) Prior Publication Data

US 2024/0078637 A1 Mar. 7, 2024

(30) Foreign Application Priority Data

Sep. 7, 2022 (CN) ......................... 202211088247.4

(51) Int. Cl.
*G06T 5/50* (2006.01)
*A61B 8/00* (2006.01)
(Continued)

(52) U.S. Cl.
CPC .............. *G06T 5/50* (2013.01); *A61B 8/0841* (2013.01); *A61B 8/5246* (2013.01); *G06T 3/60* (2013.01);
(Continued)

(58) Field of Classification Search
None
See application file for complete search history.

(56) References Cited

U.S. PATENT DOCUMENTS

2014/0187942 A1* 7/2014 Wang .................. A61B 8/0841 600/439
2016/0317118 A1 11/2016 Parthasarathy et al.
2020/0178927 A1* 6/2020 Patton .................. A61B 8/0841

FOREIGN PATENT DOCUMENTS

CN 102920476 A * 2/2013
CN 106388911 A 2/2017
(Continued)

OTHER PUBLICATIONS

Fu Jilin, Yan Guixia, & Ling Feng (2016). Ultrasound Needle Enhancement System Based on Radon Transform. China Medical Device Information, 22(7), 58-62.*
(Continued)

*Primary Examiner* — Andrew W Bee
*Assistant Examiner* — Christine Zhao
(74) *Attorney, Agent, or Firm* — METIS IP LLC

(57) ABSTRACT

The present disclosure provides systems and methods for ultrasound image processing. The methods include obtaining a first ultrasound image and a second ultrasound image of a target subject. The first ultrasound image and the second ultrasound image include a linear interventional device within the target subject. The methods include identifying one or more line segments in the second ultrasound image by processing the second ultrasound image using a first line detection algorithm. For each of the one or more line segments, the methods include determining a corrected line segment by processing a target region in the second ultrasound image corresponding to the line segment using a second line detection algorithm. The methods include generating a fused ultrasound image of the first ultrasound image and the second ultrasound image based on one or more corrected line segments corresponding to the one or more line segments.

20 Claims, 14 Drawing Sheets

(51) Int. Cl.

| | |
|---|---|
| ***A61B 8/08*** | (2006.01) |
| ***G06T 3/60*** | (2006.01) |
| ***G06T 5/10*** | (2006.01) |
| ***G06T 5/20*** | (2006.01) |
| ***G06T 7/12*** | (2017.01) |

(52) U.S. Cl.
CPC .................. *G06T 5/10* (2013.01); *G06T 5/20* (2013.01); *G06T 7/12* (2017.01); *G06T 2207/10132* (2013.01); *G06T 2207/20061* (2013.01); *G06T 2207/20221* (2013.01); *G06T 2207/30004* (2013.01)

(56) References Cited

FOREIGN PATENT DOCUMENTS

| | | | | | |
|---|---|---|---|---|---|
| CN | 109431584 | A | | 3/2019 | |
| CN | 109447067 | A | * | 3/2019 | ....... G06F 18/23213 |
| CN | 110251210 | A | | 9/2019 | |
| CN | 111110332 | A | | 5/2020 | |
| CN | 111476790 | A | * | 7/2020 | ............... G06T 7/13 |
| CN | 113724277 | A | | 11/2021 | |
| CN | 118674720 | A | * | 9/2024 | ............. G06V 10/26 |
| WO | 2017092454 | A1 | | 6/2017 | |
| WO | 2018053739 | A1 | | 3/2018 | |

OTHER PUBLICATIONS

Jayasree Chakraborty, Abhishek Midya, Sudipta Mukhopadhyay, Rangaraj M. Rangayyan, Anup Sadhu, Veenu Singla, Niranjan Khandelwal, Pinakpani Bhattacharyya, & Paulo M. Azevedo-Marques (2015). Detection of the nipple in mammograms with Gabor filters and the Radon transform. Biomedical Signal Processing and Control.*

Cheung, S., & Rohling, R. (2004). Enhancement of needle visibility in ultrasound-guided percutaneous procedures. Ultrasound in medicine & biology, 30(5), 617-624. https://doi.org/10.1016/j.ultrasmedbio.2004.02.001.*

Guang-Quan Zhou, Phoebe Chan, & Yong-Ping Zheng (2015). Automatic measurement of pennation angle and fascicle length of gastrocnemius muscles using real-time ultrasound imaging. Ultrasonics, 57, 72-83.*

Fu, Jilin et al., Ultrasound Needle Enhancement System Based on Radon Transform, China Medical Device Information, 58-62, 2016.

Yu, Ming et al., A License Plate Tilt Correction Algorithm Combined Hough and Radon Transform, Control Engineering of China, 20(6): 1014-1017, 2013.

Lu, Jun et al., Compute Slanting Degree of the Stored-grain Insects Image Based on Radon Transform, journal of agricultural mechanization research, 5: 39-41, 2007.

* cited by examiner

400

802

804

810

820

Sheet 10 of 14

804

840

850

860

906

SYSTEMS AND METHODS FOR ULTRASOUND IMAGE PROCESSING

CROSS-REFERENCE TO RELATED APPLICATIONS

This application claims priority to Chinese Patent Application No. 202211088247.4, filed on Sep. 7, 2022, the contents of which are incorporated herein by reference.

TECHNICAL FIELD

The present disclosure generally relates to the imaging field, and more particularly, relates to systems and methods for ultrasound image processing.

BACKGROUND

Medical imaging techniques have been widely used in a variety of fields including, e.g., medical treatments and/or diagnosis. For example, an ultrasonic technique can be used to assist doctors in interventional operations (e.g., puncture biopsy). When an interventional operation is performed, a linear interventional device (e.g., a puncture needle) needs to be inserted into a target region of a patient, and some body parts of the patient (e.g., nerve tissues) that cannot be punctured need to be avoided. Through the ultrasonic technique, a position of the linear interventional device within the patient can be imaged in real time, which can improve the efficiency, accuracy, and safety of the interventional operation.

Since the linear interventional device usually has a smooth surface, specular reflection of ultrasonic waves occurs at the smooth surface of the linear interventional device during the propagation of the ultrasonic waves, which weakens reflected ultrasonic waves and reduces the imaging quality with respect to the linear interventional device in the ultrasound image. Therefore, it is desirable to provide systems and methods for ultrasound image processing, which can improve the imaging quality of a linear interventional device in an ultrasound image.

SUMMARY

In an aspect of the present disclosure, a method for image processing is provided. The method may be implemented on a computing device having at least one processor and at least one storage device. The method may include obtaining a first ultrasound image and a second ultrasound image of a target subject. The first ultrasound image and the second ultrasound image may include a linear interventional device within the target subject, the first ultrasound image and the second ultrasound image may be captured by emitting different ultrasonic waves toward the target subject, and the second ultrasound image may have a better imaging quality with respect to the linear interventional device than the first ultrasound image. The method may include identifying one or more line segments in the second ultrasound image by processing the second ultrasound image using a first line detection algorithm. For each of the one or more line segments, the method may also include determining a corrected line segment by processing a target region in the second ultrasound image corresponding to the line segment using a second line detection algorithm. The method may further include generating a fused ultrasound image of the first ultrasound image and the second ultrasound image based on one or more corrected line segments corresponding to the one or more line segments.

In some embodiments, the first ultrasound image may be captured by emitting ultrasonic waves toward the target subject along a first angle with respect to an insertion direction of the linear interventional device, the second ultrasound image may be captured by emitting ultrasonic waves toward the target subject along a second angle with respect to the insertion direction of the linear interventional device, and the second angle may be closer to 90 degrees than the first angle.

In some embodiments, the first line detection algorithm may include at least one of a Hough transform algorithm, a region growing algorithm, or a machine learning algorithm.

In some embodiments, the second line detection algorithm may include at least one of a Radon transform algorithm or a Gabor filtering algorithm.

In some embodiments, the first line detection algorithm may be a Hough transform algorithm, and the identifying one or more line segments in the second ultrasound image by processing the second ultrasound image using a first line detection algorithm may include generating a binary image by performing a binary operation on at least a portion of the second ultrasound image; obtaining one or more lines by processing the binary image using the Hough transform algorithm; for each of the one or more lines, determining, in the binary image, a plurality of pixel points that correspond to the linear interventional device and are located on the line; and determining a line segment corresponding to the line based on the plurality of pixel points.

In some embodiments, for each of the one or more line segments, the determining a corrected line segment by processing a target region in the second ultrasound image corresponding to the line segment using a second line detection algorithm may include, for each of the one or more line segments, generating a plurality of rotation images by rotating the target region; for each of the plurality of rotation images, determining a sum of pixel values on each row of the rotation image; determining a target row with a maximum sum among a plurality of rows in the plurality of rotation images and a rotation angle of the rotation image corresponding to the target row; and determining the corrected line segment based on the target row and the rotation angle.

In some embodiments, the generating a plurality of rotation images by rotating the target region may include obtaining a filtered image by filtering the target region using a Gabor filtering algorithm; and generating the plurality of rotation images by rotating the filtered image.

In some embodiments, the generating a fused ultrasound image of the first ultrasound image and the second ultrasound image based on one or more corrected line segments corresponding to the one or more line segments may include for each of the one or more corrected line segments, determining an image window corresponding to the corrected line segment from the second ultrasound image based on an angle of the corrected line segment in the second ultrasound image; determining a target weight of the image window, the target weight being associated with a probability that the corrected line segment corresponds to the linear interventional device; and generating the fused ultrasound image by fusing the first ultrasound image and the image window of each corrected line segment based on the target weight.

In some embodiments, the determining a target weight of the image window may include obtaining an initial weight of the image window; generating a plurality of vertical lines on the corrected line segment corresponding to the image window; determining whether pixel values of a plurality of pixel points on each of the plurality of vertical lines satisfy a first preset condition; in response to determining that the first preset condition is satisfied, determining the target weight of the image window based on the initial weight of the image window and a preset coefficient.

In some embodiments, the generating the fused ultrasound image by fusing the first ultrasound image and the image window of each corrected line segment based on the target weight may include for each corrected line segment, determining a sub-weight of each pixel point in the image window corresponding to the corrected line segment based on the target weight of the image window; determining a weighted image window by processing each pixel point in the image window based on the sub-weight of each pixel point; and generating the fused ultrasound image by fusing the first ultrasound image and the weighted image window of each corrected line segment.

In some embodiments, the method may further include obtaining a third ultrasound image of the linear interventional device captured after the first ultrasound image and the second ultrasound image; determining whether the third ultrasound image satisfies a second preset condition; in response to determining that the third ultrasound image satisfies the second preset condition, generating a second fused image of the third ultrasound image and the second ultrasound image based on the corrected line segment corresponding to each of the one or more line segments; or in response to determining that the third ultrasound image does not satisfy the second preset condition, obtaining a fourth ultrasound image having a better imaging quality with respect to the linear interventional device than the third ultrasound image for generating the second fused image.

In another aspect of the present disclosure, a system for ultrasound image processing is provided. The system may include at least one storage device including a set of instructions; and at least one processor configured to communicate with the at least one storage device. When executing the set of instructions, the at least one processor may be configured to direct the system to perform operations. The operations may include obtaining a first ultrasound image and a second ultrasound image of a target subject. The first ultrasound image and the second ultrasound image may include a linear interventional device within the target subject, the first ultrasound image and the second ultrasound image may be captured by emitting different ultrasonic waves toward the target subject, and the second ultrasound image may have a better imaging quality with respect to the linear interventional device than the first ultrasound image. The operations may include identifying one or more line segments in the second ultrasound image by processing the second ultrasound image using a first line detection algorithm. For each of the one or more line segments, the operations may include determining a corrected line segment by processing a target region in the second ultrasound image corresponding to the line segment using a second line detection algorithm. The operations may include generating a fused ultrasound image of the first ultrasound image and the second ultrasound image based on one or more corrected line segments corresponding to the one or more line segments.

In still another aspect of the present disclosure, a non-transitory computer readable medium is provided. The non-transitory computer readable medium may comprise executable instructions that, when executed by at least one processor, direct the at least one processor to perform a method. The method may include obtaining a first ultrasound image and a second ultrasound image of a target subject. The first ultrasound image and the second ultrasound image may include a linear interventional device within the target subject, the first ultrasound image and the second ultrasound image may be captured by emitting different ultrasonic waves toward the target subject, and the second ultrasound image may have a better imaging quality with respect to the linear interventional device than the first ultrasound image. The method may include identifying one or more line segments in the second ultrasound image by processing the second ultrasound image using a first line detection algorithm. For each of the one or more line segments, the method may also include determining a corrected line segment by processing a target region in the second ultrasound image corresponding to the line segment using a second line detection algorithm. The method may further include generating a fused ultrasound image of the first ultrasound image and the second ultrasound image based on one or more corrected line segments corresponding to the one or more line segments.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1A:
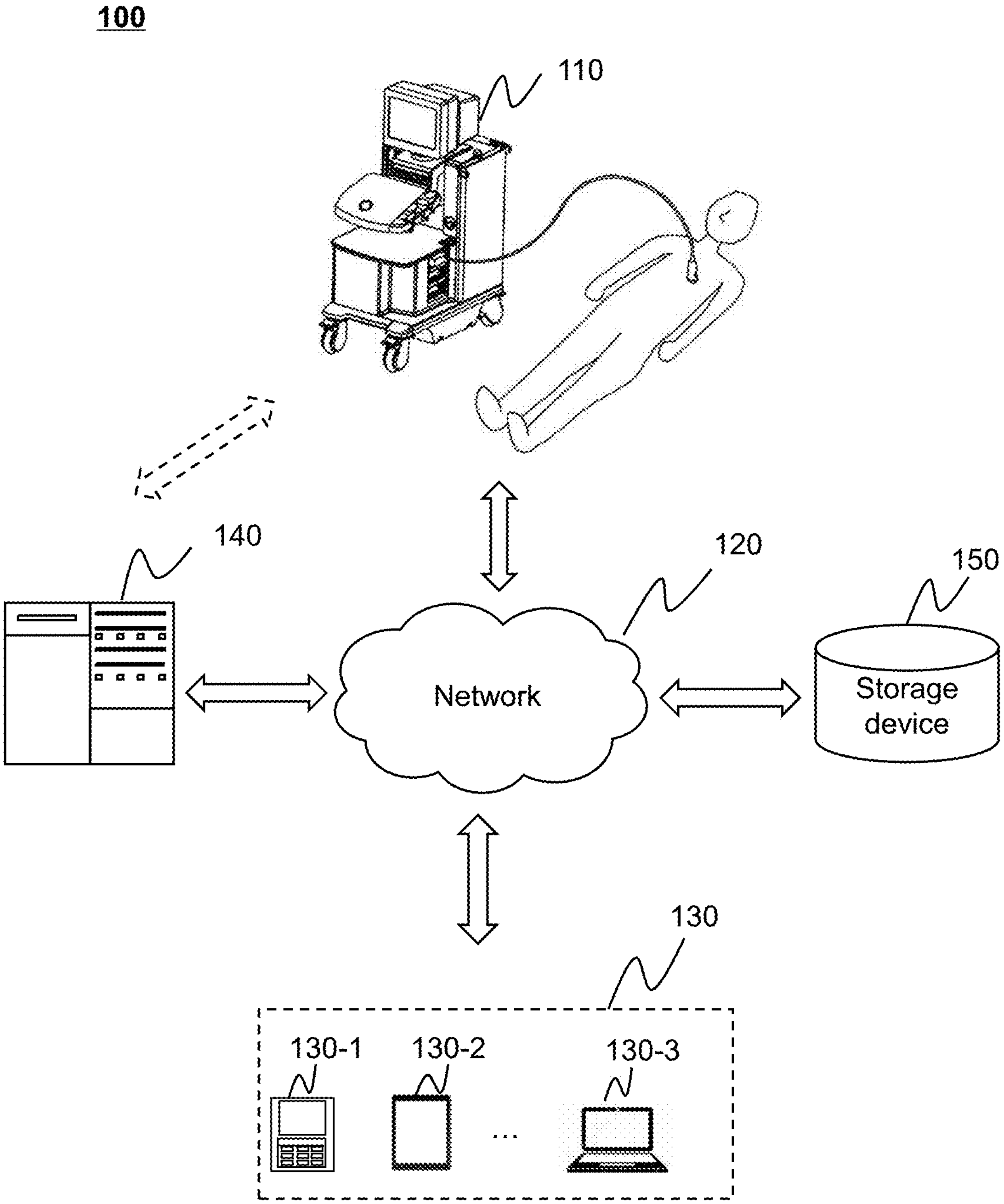
FIG. 1A is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging/treatment, such as for disease diagnostic, disease therapy, or research purposes. In some embodiments, the systems may include an imaging system. The imaging system may include a single modality system and/or a multi-modality system. The term "modality" used herein broadly refers to an imaging or treatment method or technology that gathers, generates, processes, and/or analyzes imaging information of a subject or treatments the subject. The single modality system may include, for example, an ultrasound imaging system, an X-ray imaging system, a computed tomography (CT) system, a magnetic resonance imaging (MRI) system, an ultrasonography system, a positron emission tomography (PET) system, an optical coherence tomography (OCT) imaging system, an ultrasound imaging system, an intravascular ultrasound (IVUS) imaging system, a near-infrared spectroscopy (NIRS) imaging system, or the like, or any combination thereof. The multi-modality system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, etc. It should be noted that the medical system described below is merely provided for illustration purposes, and not intended to limit the scope of the present disclosure.

The term "pixel" and "voxel" in the present disclosure are used interchangeably to refer to an element in an image. In the present disclosure, the term "image" may refer to a two-dimensional (2D) image, a three-dimensional (3D) image, or a four-dimensional (4D) image (e.g., a time series of 3D images). In some embodiments, the term "image" may refer to an image of a region (e.g., a region of interest (ROI)) of a subject. In some embodiment, the image may be a medical image, an optical image, etc.

In the present disclosure, a representation of a subject (e.g., an object, a patient, or a portion thereof) in an image may be referred to as "subject" for brevity. For instance, a representation of an organ, tissue (e.g., a heart, a liver, a lung), or an ROI in an image may be referred to as the organ, tissue, or ROI, for brevity. Further, an image including a representation of a subject, or a portion thereof, may be referred to as an image of the subject, or a portion thereof, or an image including the subject, or a portion thereof, for brevity. Still further, an operation performed on a representation of a subject, or a portion thereof, in an image may be referred to as an operation performed on the subject, or a portion thereof, for brevity. For instance, a segmentation of a portion of an image including a representation of an ROI from the image may be referred to as a segmentation of the ROI for brevity.

For illustration purposes, the present disclosure mainly describes systems and methods relating to ultrasound imaging. It should be noted that the ultrasound imaging system described below is merely provided as an example, and not intended to limit the scope of the present disclosure. The systems and methods disclosed herein may be applied to process images acquired using any other imaging modalities.

In an interventional operation, ultrasound imaging technique is often used to capture real-time ultrasound images to track the position of a linear interventional device. However, the imaging effect of the linear interventional device is poor due to specular reflection of ultrasonic waves occurs at the smooth surface of the linear interventional device. The linear interventional device needs to be detected from the ultrasound images for post-processing the ultrasound images.

Conventionally, the determination (e.g., positioning) of a linear interventional device in an ultrasound image is always performed using a Hough transform algorithm. The Hough transform algorithm has a high sensitivity, which can improve the efficiency of the determination of the linear interventional device. However, the Hough transform algorithm have a limited accuracy. For example, a detection result generated based on the Hough transform algorithm includes lines corresponding to the linear interventional device (e.g., a puncture needle) and/or normal tissues, which reduces the accuracy of the determination (e.g., positioning) of the linear interventional device in the ultrasound image.

The present disclosure provides systems and methods for ultrasound image processing that can improve the line detection accuracy (i.e., the detection accuracy of linear interventional device) and improve the imaging effect of the linear interventional device in ultrasound images). The methods may include obtaining a first ultrasound image and a second ultrasound image of a target subject. The first ultrasound image and the second ultrasound image may include a linear interventional device within the target subject. The first ultrasound image and the second ultrasound image may be captured by emitting different ultrasonic waves toward the target subject, and the second ultrasound image may have a better imaging quality with respect to the linear interventional device than the first ultrasound image. The methods may also include identifying one or more line segments in the second ultrasound image by processing the second ultrasound image using a first line detection algorithm. For each of the one or more line segments, the methods may include determining a corrected line segment by processing a target region in the second ultrasound image corresponding to the line segment using a second line detection algorithm. The methods may further include generating a fused ultrasound image of the first ultrasound image and the second ultrasound image based on one or more corrected line segments corresponding to the one or more line segments.

By using the first line detection algorithm and the second line detection algorithm, a coarse line detection and a fine line detection can be consecutively performed to determine the one or more corrected line segments. In some embodiments, the first line detection algorithm may include the Hough transform algorithm, a region growing algorithm, a machine learning algorithm, etc., which may have advantages, such as a high sensitivity, a high recall rate, a small amount of calculation, easy operation(s), etc. The second line detection algorithm may include a Radon transform algorithm, a Gabor filtering algorithm, etc., which may have a high accuracy. By using the second line detection algorithm to process one or more target regions in the second ultrasound image corresponding to the one or more line segments that are identified using the first line detection algorithm, the advantages of the first line detection algorithm and the second line detection algorithm can be combined, thereby improving the efficiency and accuracy of the line detection.

In addition, the fused ultrasound image of the first ultrasound image and the second ultrasound image can be generated based on the one or more corrected line segments corresponding to the one or more line segments, which includes the position information of the linear interventional device in the first ultrasound image and the image data of the linear interventional device in the second ultrasound image. Therefore, the fused ultrasound image can provide the real-time position information of the linear interventional device within the target subject, and the relatively good imaging quality with respect to the linear interventional device, thereby improving the accuracy of the determination of the linear interventional device, and improving the accuracy and reliability of the diagnosis and/or treatment.

FIG. 1A is a schematic diagram illustrating an exemplary image processing system 100 according to some embodiments of the present disclosure. For illustration purposes, the image processing system 100 illustrated in FIG. 1A may be an ultrasound imaging system. As shown in FIG. 1A, the ultrasound imaging system may include an ultrasound imaging device 110, a network 120, one or more terminals 130, a processing device 140, and a storage device 150. In some embodiments, the ultrasound imaging device 110, the processing device 140, the storage device 150, and/or the terminal(s) 130 may be connected to and/or communicate with each other via a wireless connection (e.g., the network 120), a wired connection, or a combination thereof. The connection between the components in the image processing system 100 may be variable.

The ultrasound imaging device 110 may be configured to generate or provide image data by scanning a target subject or at least a portion of the target subject. For example, the ultrasound imaging device 110 may capture image data (e.g., ultrasonic image data, ultrasonic images, etc.) of the target subject by emitting ultrasonic waves toward the target subject. In some embodiments, the ultrasound imaging device 110 may include an ultrasonic probe (also referred to as an ultrasonic transducer). The ultrasonic probe may be configured to transmit and/or receive the ultrasonic waves. For example, the ultrasonic probe may include an ultrasonic transmitter and an ultrasonic receiver, wherein the ultrasonic transmitter is configured to convert first electrical signals into ultrasonic waves and emit the ultrasonic waves toward the target subject, and the ultrasonic receiver is configured to receive reflected ultrasonic waves from the target subject and convert the reflected ultrasonic waves into second electrical signals. As another example, the ultrasonic probe may include an ultrasonic transceiver that can be configured to emit the ultrasonic waves toward the target subject and receive the reflected ultrasonic waves from the target subject. Exemplary ultrasonic probes may include a magnetostriction probe, a piezoelectric probe, a capacitive probe, a micromachined probe, an interdigital probe, or the like, or any combination thereof. In some embodiments, the ultrasonic waves may be defined by a plurality of parameters. Exemplary parameters may include a frequency (or a wave length), a power, a power density, a direction, or the like, or any combination thereof. For example, the ultrasound imaging device 110 (e.g., the ultrasonic probe of the ultrasound imaging device 110) may emit different ultrasonic waves with different parameters according to a preset plan (e.g., a treatment plan).

In some embodiments, the ultrasound imaging device 110 may be used to scan the target subject in an interventional operation, which may be performed on the target subject using an interventional device. The interventional device refers to a device that can be inserted into the target subject for diagnosing and/or treating the target subject. For example, the interventional device may be a puncture needle that is used to sample a tissue from the target subject or inject a liquid into the target subject. In some embodiments, the interventional device may include a linear interventional device (e.g., the puncture needle, a guiding catheter, etc.) and/or a nonlinear interventional device (e.g., a guidewire, a stent, etc.). As used herein, if at least a portion of an interventional device is linear or approximately linear, the interventional device may be regarded as a linear interventional device.

Figure 1B:
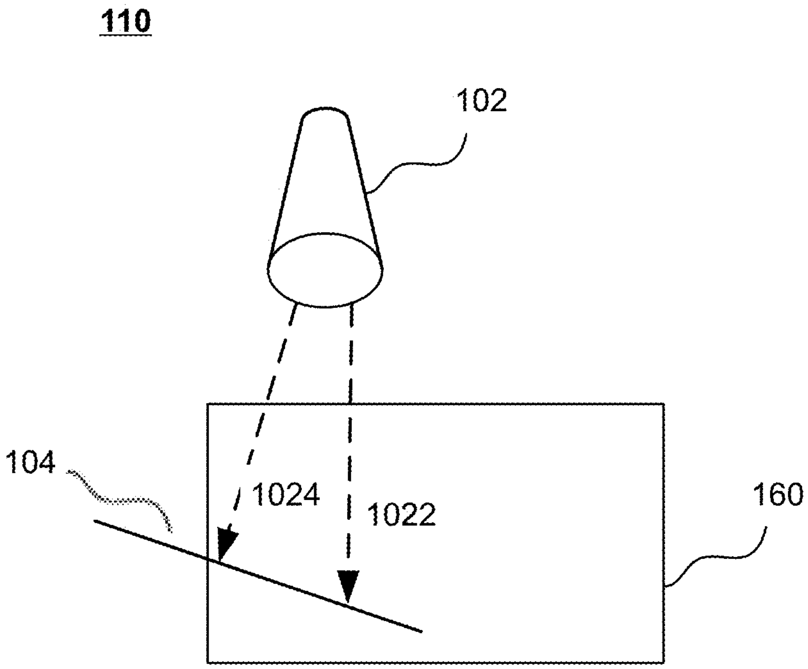
FIG. 1B is a schematic diagram illustrating an exemplary ultrasound imaging device according to some embodiments of the present disclosure.

Merely by way of example, as illustrated in FIG. 1B, the ultrasound imaging device 110 may include an ultrasonic probe 102 used to capture ultrasound images of a linear interventional device (e.g., the puncture needle) 104. The linear interventional device 104 is inserted into the target subject 160 (e.g., a target region of the target subject) at a preset angle (e.g., an insertion direction). The ultrasonic probe 102 emits ultrasonic waves 1022 and ultrasonic waves 1024 toward the target subject, respectively, wherein the ultrasonic waves 1022 are emitted along a first angle with respect to the insertion direction of the linear interventional device 104, the ultrasonic waves 1024 are emitted along a second angle with respect to the insertion direction of the linear interventional device 104, and the second angle is closer to 90 degrees than the first angle. Correspondingly, a first ultrasound image is captured based on the ultrasonic waves 1022 (e.g., corresponding reflected ultrasonic waves), and a second ultrasound image is captured based on the ultrasonic waves 1024 (e.g., corresponding reflected ultrasonic waves).

The target subject may include patients or other experimental subjects (e.g., experimental mice or other animals). In some embodiments, the target subject may be a patient or a specific portion, organ, and/or tissue of the patient. For example, the target subject may include the head, the neck, the thorax, the heart, the stomach, a blood vessel, soft tissue, a tumor, nodules, or the like, or any combination thereof. In some embodiments, the target subject may be non-biological. For example, the target subject may include a phantom, a man-made object, etc. The terms "object" and "subject" are used interchangeably in the present disclosure.

The network 120 may include any suitable network that can facilitate the exchange of information and/or data for the image processing system 100. In some embodiments, one or more components (e.g., the ultrasound imaging device 110, the terminal 130, the processing device 140, the storage device 150, etc.) of the image processing system 100 may communicate information and/or data with one or more other components of the image processing system 100 via the network 120. In some embodiments, the network 120 may include one or more network access points.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the terminal(s) 130 may include a processing unit, a display unit, a sensing unit, an input/output (I/O) unit, a storage unit, etc. In some embodiments, the terminal(s) 130 may be part of the processing device 140.

The processing device 140 may process data and/or information obtained from one or more components (e.g., the ultrasound imaging device 110, the terminal(s) 130, and/or the storage device 150) of the image processing system 100. For example, the processing device 140 may perform line detection on an ultrasound image to detect a linear interventional device in the ultrasound image. As another example, the processing device 140 may generate a fused ultrasound image by fusing multiple ultrasound images. In some embodiments, the processing device 140 may be a single server or a server group. The server group may be centralized or distributed. In some embodiments, the processing device 140 may be local or remote. In some embodiments, the processing device 140 may be implemented on a cloud platform.

In some embodiments, the processing device 140 may be implemented by a computing device. For example, the computing device may include a processor, a storage, an input/output (I/O), and a communication port. In some embodiments, the processing device 140, or a portion of the processing device 140 may be implemented by a portion of the terminal 130.

The storage device 150 may store data/information obtained from the ultrasound imaging device 110, the terminal(s) 130, and/or any other component of the image processing system 100. In some embodiments, the storage device 150 may include a mass storage, a removable storage, a volatile read-and-write memory, a read-only memory (ROM), or the like, or any combination thereof. In some embodiments, the storage device 150 may store one or more programs and/or instructions to perform exemplary methods described in the present disclosure.

In some embodiments, the image processing system 100 may include one or more additional components and/or one or more components of the image processing system 100 described above may be omitted. Additionally or alternatively, two or more components of the image processing system 100 may be integrated into a single component. A component of the image processing system 100 may be implemented on two or more sub-components.

Figure 2:
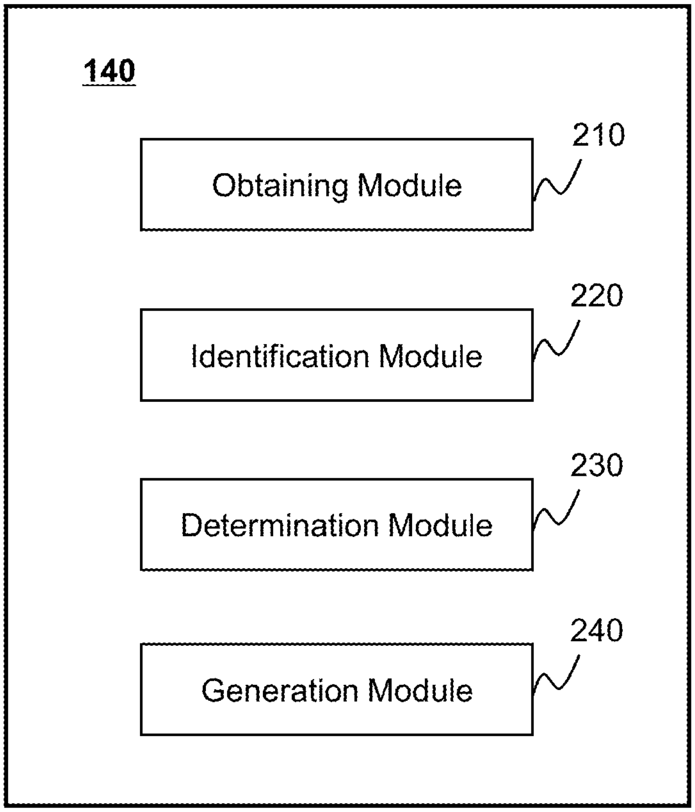
FIG. 2 is a block diagram illustrating an exemplary processing device according to some embodiments of the present disclosure.

FIG. 2 is a block diagram illustrating an exemplary processing device 140 according to some embodiments of the present disclosure. In some embodiments, the processing device 140 may be in communication with a computer-readable storage medium (e.g., the storage device 150 illustrated in FIG. 1A) and execute instructions stored in the computer-readable storage medium. The processing device 140 may include an obtaining module 210, an identification module 220, a determination module 230, and a generation module 240.

The obtaining module 210 may be configured to obtain a first ultrasound image and a second ultrasound image of a target subject. The first ultrasound image and the second ultrasound image may include a linear interventional device within the target subject. The linear interventional device refers to a device that can be inserted into the target subject for diagnosing and/or treating the target subject, and at least a portion of the device is linear or approximately linear. The first ultrasound image and the second ultrasound image may be captured by emitting different ultrasonic waves toward the target subject. In some embodiments, the second ultrasound image may have a better imaging quality with respect to the linear interventional device than the first ultrasound image. More descriptions regarding the obtaining the first ultrasound image and the second ultrasound image may be found elsewhere in the present disclosure. See, e.g., operation 302 and relevant descriptions thereof.

The identification module 220 may be configured to identify one or more line segments in the second ultrasound image by processing the second ultrasound image using a first line detection algorithm. A line segment refers to a candidate representation of the linear interventional device in the second ultrasound image. The first line detection algorithm may be able to detect most of straight lines in an image. More descriptions regarding the identification of the one or more line segments in the second ultrasound image may be found elsewhere in the present disclosure. See, e.g., operation 304 and relevant descriptions thereof.

The determination module 230 may be configured to, for each of the line segment(s), determine a corrected line segment by processing a target region in the second ultrasound image corresponding to the line segment using a second line detection algorithm. A corrected line segment refers to a target representation of the linear interventional device in the second ultrasound image. The second line detection algorithm may have a relatively high line detection accuracy. More descriptions regarding the determination of the one or more corrected line segments in the second ultrasound image may be found elsewhere in the present disclosure. See, e.g., operation 306 and relevant descriptions thereof.

The generation module 240 may be configured to generate a fused ultrasound image of the first ultrasound image and the second ultrasound image based on one or more corrected line segments corresponding to the line segment(s). The fused ultrasound image refers to an image that fuses the first ultrasound image and the second ultrasound image. More descriptions regarding the generation of the fused ultrasound image may be found elsewhere in the present disclosure. See, e.g., operation 308 and relevant descriptions thereof.

In some embodiments, the processing device 140 may include one or more other modules, one or more modules mentioned above can be omitted. For example, the processing device 140 may include a storage module to store data generated by the modules in the processing device 140. In some embodiments, any two of the modules may be combined as a single module, and any one of the modules may be divided into two or more units.

Figure 3:
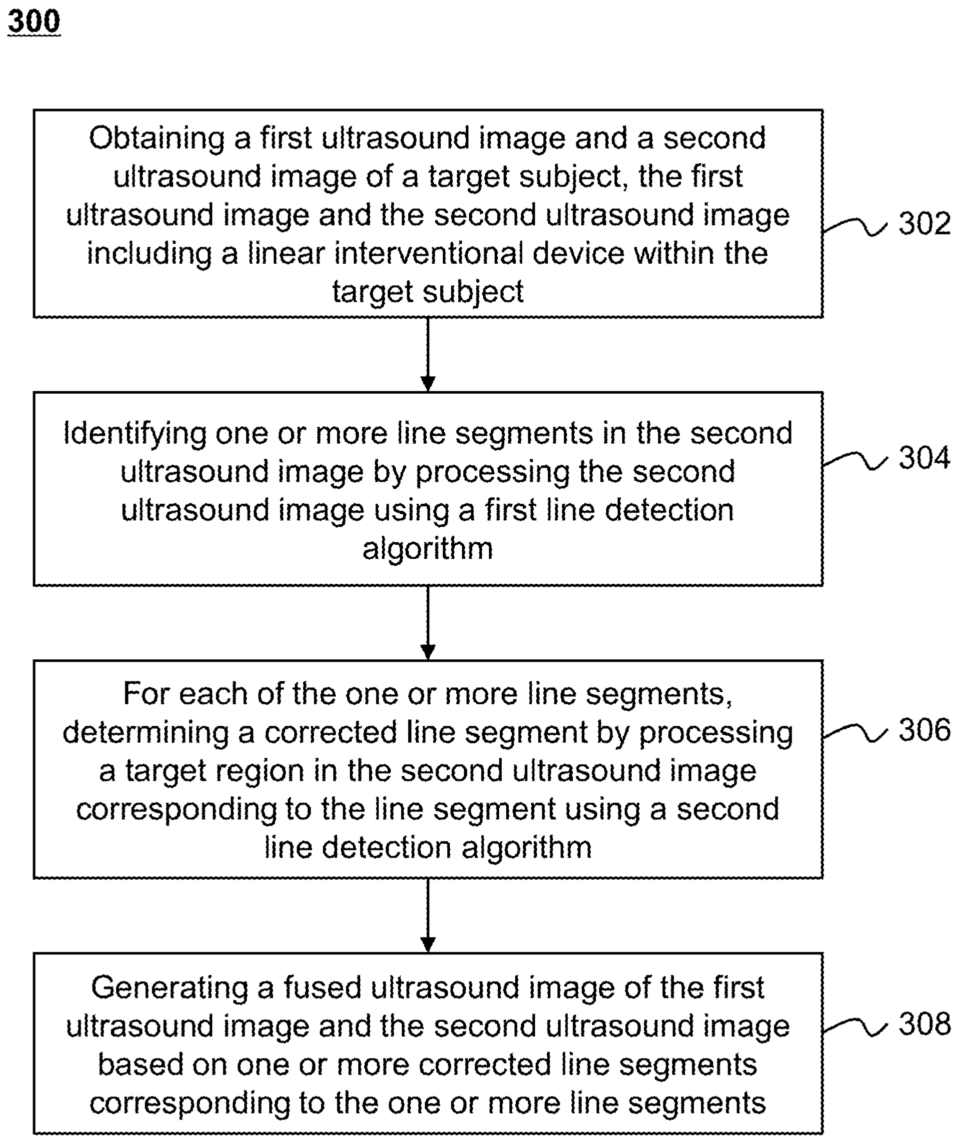
FIG. 3 is a flowchart illustrating an exemplary process for generating a fused ultrasound image according to some embodiments of the present disclosure.

FIG. 3 is a flowchart illustrating an exemplary process for generating a fused ultrasound image according to some embodiments of the present disclosure. Process 300 may be implemented in the image processing system 100 illustrated in FIG. 1A. For example, the process 300 may be stored in the storage device 150 in the form of instructions (e.g., an application), and invoked and/or executed by the processing device 140.

In 302, the processing device 140 (e.g., the obtaining module 210) may obtain a first ultrasound image and a second ultrasound image of a target subject.

In some embodiments, the first ultrasound image and the second ultrasound image may include a linear interventional device within the target subject. The linear interventional device refers to a device that can be inserted into the target subject for diagnosing and/or treating the target subject, and at least a portion of the device is linear or approximately linear. For example, the linear interventional device may be a puncture needle that is used to sample a tissue from the target subject or inject a liquid into the target subject. In some embodiments, when the linear interventional device has been inserted into the target subject (e.g., a target region of the target subject), ultrasound images of the target subject may include visual representations of the linear interventional device. For example, the first ultrasound image and the second ultrasound image may include visual representations (e.g., a straight line) corresponding to the linear interventional device.

The first ultrasound image and the second ultrasound image may be captured by emitting different ultrasonic waves toward the target subject. For example, the first ultrasound image may be captured by emitting first ultrasonic waves toward the target subject, the second ultrasound image may be captured by emitting second ultrasonic waves toward the target subject, and the first ultrasonic waves may be different from the second ultrasonic waves. As used herein, when at least one parameter (e.g., a frequency (or a wave length), a power, a power density, a direction, etc.) of the first ultrasonic waves is different from the at least one parameter of the second ultrasonic waves, the first ultrasonic waves may be deemed as being different from the second ultrasonic waves. It should be noted that the linear interventional device is still or approximately still during a time period from a time point when the first ultrasound image is captured to a time point when the second ultrasound image is captured. For example, the first ultrasound image and the second ultrasound image are captured in a short time period, while the linear interventional device may be still in the short time period.

Merely by way of example, the first ultrasound image may be captured by emitting first ultrasonic waves toward the target subject along a first angle with respect to an insertion direction of the linear interventional device, the second ultrasound image may be captured by emitting second ultrasonic waves toward the target subject along a second angle with respect to the insertion direction of the linear interventional device, and the second angle may be different from the first angle. That is, the direction of the first ultrasonic waves with respect to the linear interventional device may be different from that of the second ultrasonic waves. The insertion direction refers to a direction along which the linear interventional device is inserted into the target subject. As another example, the first ultrasound image may be captured by emitting the first ultrasonic waves with a first frequency range, the second ultrasound image may be captured by emitting the second ultrasonic waves with a second frequency range, and the second frequency range may be different from the first frequency range. That is, the frequency of the first ultrasonic waves may be different from the frequency of the second ultrasonic waves.

In some embodiments, the second ultrasound image may have a better imaging quality with respect to the linear interventional device than the first ultrasound image. The "better imaging quality" may indicate that an imaging quality of a second representation of the linear interventional device in the second ultrasound image is better than an imaging quality of a first representation of the linear interventional device in the second ultrasound image. For example, a definition or a resolution of the second representation may be higher than a definition or a resolution of the first representation. As another example, artifact(s) or noise(s) of the second representation may be less than artifact(s) or noise(s) of the first representation.

Merely by way of example, the second angle with respect to the insertion direction of the linear interventional device may be closer to 90 degrees than the first angle. That is, the direction of the second ultrasonic waves may be more perpendicular to the insertion direction of the linear interventional device than the direction of the first ultrasonic waves.

For instance, the first ultrasound image (also referred to as a scanning frame) may be captured by emitting the first ultrasonic waves toward the target subject along a preset direction, and the second ultrasound image (also referred to as a deflection frame) may be captured by emitting the second ultrasonic waves toward the target subject along a direction deflected from the preset direction (also referred to as a deflection direction). The preset direction refers to a direction that is perpendicular to a surface of an ultrasonic probe of an ultrasound imaging device (e.g., the ultrasonic probe 102 of the ultrasound imaging device 110) and has a preset inclination angle with the insertion direction of the linear interventional device. The deflection direction refers to a direction that deviates at a preset angle from the preset direction. For example, the preset angle may include 10 degrees, 20 degrees, 30 degrees, 40 degrees, etc. As another example, the deflection direction may be approximately perpendicular to the insertion direction of the linear interventional device. The "approximately perpendicular to the insertion direction of the linear interventional device" refers to that an included angle between the deflection direction and the insertion direction of the linear interventional device is within an angle range from (90-M) degrees to (90+AA) degrees, wherein AA refers to a preset angle error. Sine a reflection of the ultrasonic waves with respect to the linear interventional device (e.g., the puncture needle) is usually a specular reflection, the second ultrasonic waves that are perpendicular to the insertion direction of the linear interventional device may result in less specular reflection, so that the second ultrasound image may have the better imaging quality with respect to the linear interventional device than the first ultrasound image.

As another example, the power density of the second ultrasonic waves may be larger than the power density of the first ultrasonic waves, and the second ultrasound image may have the better imaging quality with respect to the linear interventional device than the first ultrasound image.

In some embodiments, the different ultrasonic waves may be emitted by one or more ultrasound imaging devices. For example, a same ultrasound imaging device (e.g., the ultrasound imaging device 110) may emit the first ultrasonic waves and the second ultrasonic waves. As another example, a first ultrasound imaging device may emit the first ultrasonic waves, and a second ultrasound imaging device may emit the second ultrasonic waves.

In some embodiments, the processing device 140 may obtain the first ultrasound image and/or the second ultrasound image from an imaging device (e.g., the ultrasound imaging device 110, etc.) or a storage device (e.g., the storage device 150, a database, or an external storage) that stores the first ultrasound image and/or the second ultrasound image of the target subject.

In 304, the processing device 140 (e.g., the identification module 220) may identify one or more line segments in the second ultrasound image by processing the second ultrasound image using a first line detection algorithm.

A line segment refers to a candidate representation of the linear interventional device in the second ultrasound image. For example, the line segment(s) may be identified by performing a coarse line detection on the second ultrasound image using the first line detection algorithm.

The first line detection algorithm may be able to detect most of straight lines in an image. For example, the first line detection algorithm may include a Hough transform algorithm, a region growing algorithm, a machine learning algorithm, or the like, or any combination thereof.

Taking the Hough transform algorithm as an example, the Hough transform algorithm refers to an algorithm for feature extraction, which is widely used in image analysis, image processing, computer vision, etc. The Hough transform algorithm can be used to identify features (e.g., lines) in images. For example, the Hough transform algorithm may map curves or lines with a same shape in a first coordinate space to points in a second coordinate space through a transformation between the two coordinate spaces to form peak values, and convert a problem of identifying a certain shape (e.g., a line) to a problem of determining a statistical count of peaks. For instance, the processing device 140 may generate a binary image by performing a binary operation on at least a portion of the second ultrasound image, and obtain one or more lines by processing the binary image using the Hough transform algorithm. For each of the one or more lines, the processing device 140 may determine a plurality of pixel points, in the binary image that correspond to the linear interventional device and are located on the line, and determine a line segment corresponding to the line based on the plurality of pixel points. More descriptions regarding the identification of the line segment(s) in the second ultrasound image may be found in elsewhere in the present disclosure (e.g., FIGS. 4 and 7, and the descriptions thereof).

As another example, a line detection model may be used to identify the one or more line segments in the second ultrasound image by processing the second ultrasound image. For example, the processing device 140 may input the second ultrasound image into the line detection model, and the line detection model may output the one or more line segments in the second ultrasound image. In some embodiments, the line detection model may be a trained machine learning model. Exemplary machine learning models may include a convolutional neural network (CNN) model, a recurrent neural network (RNN) model, a generative adversarial network (GAN) model, or the like, or any combination thereof. In some embodiments, the processing device 140 may obtain the line detection model from a storage device (e.g., the storage device 150) of the image processing system 100 or a third-party database. In some embodiments, the line detection model may be generated by the processing device 140 or another computing device according to the machine learning algorithm. In some embodiments, the line detection model may be generated by training an initial model using a plurality of training samples. Each of the plurality of training samples may include a sample ultrasound image (as a training input) and one or more sample line segments in the sample ultrasound image (as a training label).

By using the first line detection algorithm to perform a coarse line detection, the line segment(s) can be determined for further processing, which can reduce a processing amount of the further processing, thereby improving the efficiency of the line detection.

In 306, for each of the line segment(s), the processing device 140 (e.g., the determination module 230) may determine a corrected line segment by processing a target region in the second ultrasound image corresponding to the line segment using a second line detection algorithm.

A corrected line segment refers to a target representation of the linear interventional device in the second ultrasound image. For example, one or more corrected line segments may be determined by performing a fine line detection on one or more target regions corresponding to the line segment(s) in the second ultrasound image using the second line detection algorithm.

The second line detection algorithm may have a relatively high line detection accuracy. For example, the second line detection algorithm may include a Radon transform algorithm, a Gabor filtering algorithm, or the like, or any combination thereof. In some embodiments, a detection precision of the second line detection algorithm may be higher than a detection precision of the first line detection algorithm.

Taking the Radon transform algorithm as an example, the Radon transform algorithm can transform a line segment (or a line) in an image into a domain (also referred to as a Radon space) of a line parameter. A peak (i.e., a bright line) or a trough (i.e., a dark line) may be determined based on the line segment in the image to correspond to the line parameter. Therefore, a pixel point in the Radon space corresponds to a line segment in the image, and each pixel point in the Radon space includes abundant information. In addition, the Radon transform algorithm is used to process an integration of the line segment, which is insensitive to noise(s) and/or artifact(s) in the image, thereby improving the accuracy of line detection.

In some embodiments, for each of the line segment(s), the processing device 140 may determine the target region in the second ultrasound image corresponding to the line segment. The target region refers to an image region in the second ultrasound image where the line segment is located. For example, the target region may be an image region in the second ultrasound image including a representation of the line segment. In some embodiments, the target region may have a preset shape, such as a rectangle, a square, etc.

For each of the line segment(s), the processing device 140 may further process the target region using the second line detection algorithm to determine the corrected line segment. For example, for each of the line segment(s), the processing device 140 may generate a plurality of rotation images by rotating the target region. For each of the plurality of rotation images, the processing device 140 may determine a sum of pixel values on each row of the rotation image. The processing device 140 may determine a target row with a maximum sum among a plurality of rows in the plurality of rotation images and a rotation angle of the rotation image corresponding to the target row, and determine the corrected line segment based on the target row and the rotation angle. As another example, for each of the line segment(s), the processing device 140 may determine lines of the target region corresponding to a plurality of directions. For instance, for each of the plurality of directions, the processing device 140 may determine the lines corresponding to the direction that form the target region. For each of the plurality of directions, the processing device 140 may determine a sum of pixel values on each line of the target region. The processing device 140 may determine a target line with a maximum sum among a plurality of lines corresponding to the plurality of directions and a target angle corresponding to the target line, and determine the corrected line segment based on the target line and the target angle. More descriptions regarding the determination of the corrected line segment may be found in elsewhere in the present disclosure (e.g., FIGS. 5 and 7, and the descriptions thereof).

In 308, the processing device 140 (e.g., the generation module 240) may generate a fused ultrasound image of the first ultrasound image and the second ultrasound image based on one or more corrected line segments corresponding to the line segment(s).

The fused ultrasound image refers to an image that fuses the first ultrasound image and the second ultrasound image. For example, the fused ultrasound image may be generated by fusing, based on the one or more corrected line segments, the first ultrasound image and the second ultrasound image (e.g., a portion of the second ultrasound image) using an image fusion algorithm. Exemplary image fusion algorithms may include a weighted average fusion algorithm, a pyramid fusion algorithm, a gradient domain fusion algorithm, a wavelet transform algorithm, a structural deformation algorithm, or the like, or any combination thereof.

In some embodiments, image data of the linear interventional device (e.g., image window(s) as described below) may be extracted from the second ultrasound image based on the corrected line segment(s), and the image data may be fused with the first ultrasound image to improve the image effect of the linear interventional device in the first ultrasound image. In other words, the fused ultrasound image may include both the position information of the linear interventional device in the first ultrasound image and the image data of the linear interventional device in the second ultrasound image. In some embodiments, the fused ultrasound image may be used to determine a position of the linear interventional device. For example, the processing device 140 may determine the position of the linear interventional device in the fused ultrasound image using an image identification algorithm. Since artifacts (e.g., motion artifacts) in the fused ultrasound image are reduced or eliminated, a precise position of the linear interventional device in the fused ultrasound image may be determined.

Merely by way of example, for each of the one or more corrected line segments, the processing device 140 may determine an image window corresponding to the corrected line segment from the second ultrasound image based on an angle of the corrected line segment in the second ultrasound image, and determine a target weight of the image window. The processing device 140 may generate the fused ultrasound image by fusing the first ultrasound image and the image window of each corrected line segment based on the target weight. More descriptions regarding the generation of the fused ultrasound image may be found in elsewhere in the present disclosure (e.g., FIGS. 6 and 7, and the descriptions thereof).

In some embodiments, the processing device 140 may generate the fused ultrasound image based on the one or more corrected line segments and the first ultrasound image. For example, the processing device 140 may correct the first ultrasound image based on the one or more corrected line segments to generate the fused ultrasound image.

In some embodiments, the processing device 140 may further obtain a third ultrasound image of the linear interventional device captured after the first ultrasound image and the second ultrasound image. The third ultrasound image may be obtained in a similar manner to how the first ultrasound image is obtained. For example, the third ultrasound image may be captured by emitting third ultrasonic waves toward the target subject along a third angle with respect to the insertion direction of the linear interventional device, and the processing device 140 may obtain the third ultrasound image from an imaging device (e.g., the ultrasound imaging device 110, etc.) or a storage device (e.g., the storage device 150, a database, or an external storage) that stores the third ultrasound image. The third ultrasonic waves may be the same as or different from the first ultrasonic waves, which is not limited herein.

The processing device 140 may determine whether the third ultrasound image satisfies a preset condition. The preset condition (also referred to as a second preset condition) may indicate that a displacement of the linear interventional device does not exceed a displacement threshold, such as 0.1 millimeters (mm), 0.2 mm, 0.5 mm, 0.8 mm, 1.0 mm, 1.5 mm, 2.0 mm, 2.5 mm, 3.0 mm, etc. The displacement of the linear interventional device refers to the displacement of the linear interventional device from the capture time of the first ultrasound image to the capture time of the third ultrasound image. The displacement may be determined by analyzing positions of the linear interventional device in the first and third ultrasound images, or be determined based on a displacement scale of the linear interventional device.

When the linear interventional device is still, or the displacement of the linear interventional device that is directed to move does not exceed the displacement threshold, the processing device 140 may determine that the third ultrasound image satisfies the second preset condition, and generate a second fused image of the third ultrasound image and the second ultrasound image based on the corrected line segment corresponding to each of the line segment(s). As another example, when the displacement of the linear interventional device exceeds the displacement threshold, the processing device 140 may determine that the third ultrasound image does not satisfy the second preset condition, and obtain a fourth ultrasound image having a better imaging quality with respect to the linear interventional device than the third ultrasound image for generating the second fused image. The fourth ultrasound image may be obtained in a similar manner to how the second ultrasound image is obtained. For example, the fourth ultrasound image may be captured by emitting fourth ultrasonic waves toward the target subject along a fourth angle with respect to the insertion direction of the linear interventional device. The fourth angle may be the same as the second angle. After the fourth ultrasound image is obtained, the second fused image may be generated by fusing the third ultrasound image and the fourth ultrasound image. The third ultrasound image and the fourth ultrasound image may be fused in a similar manner to how the first ultrasound image and the second ultrasound image are fused.

In some embodiments, the displacement threshold may be determined based on a system default setting or set manually by a user (e.g., a technician, a doctor, a physicist, etc.). By determining whether the third ultrasound image satisfies the second preset condition, whether the linear interventional device is still or approximately still can be determined. When the linear interventional device is still or approximately still, the first ultrasound image and the third ultrasound image can both be corrected using the second ultrasound image, and no further deflection frames (e.g., the fourth ultrasound image) need to be obtained. Therefore, ultrasonic waves emitted toward the target subject can be reduced, which can reduce the corresponding processing amount, thereby improving the efficiency of the image processing.

In some embodiments, the processing device 140 may display the ultrasound images (e.g., the first ultrasound image, the second ultrasound image, the third ultrasound image, the fourth ultrasound image, the first fused image, the second fused image, etc.) on a display interface for a user to view and/or adjust.

According to some embodiments of the present disclosure, the line segment(s) in the second ultrasound image can be identified using the first line detection algorithm, and the one or more corrected line segment corresponding to the line segment(s) can be determined using the second line detection algorithm. The first line detection algorithm has a high sensitivity, which can improve the efficiency of the line detection. The second line detection algorithm has a high precision, which can improve the accuracy of the line detection. By combing the first line detection algorithm and the second line detection algorithm, the efficiency and accuracy of the line detection can be improved simultaneously. In addition, the fused ultrasound image of the first ultrasound image and the second ultrasound image can be generated based on the one or more corrected line segments corresponding to the line segment(s), which can provide both the position information of the linear interventional device in the first ultrasound image and the image data of the linear interventional device in the second ultrasound image, thereby improving the accuracy of the determination (e.g., positioning) of the linear interventional device, and improving the accuracy and reliability of the diagnosis and/or treatment.

Figure 4:
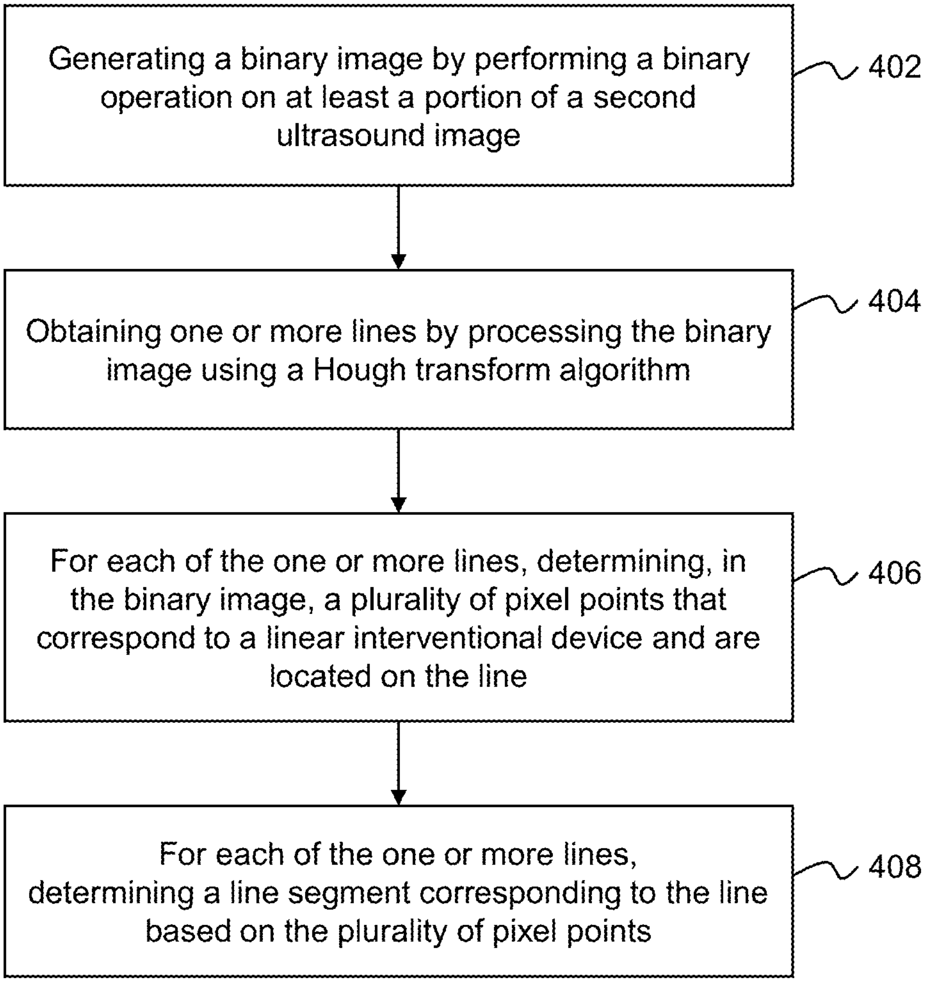
FIG. 4 is a flowchart illustrating an exemplary process for identifying one or more line segments in a second ultrasound image using a Hough transform algorithm according to some embodiments of the present disclosure.

FIG. 4 is a flowchart illustrating an exemplary process 400 for identifying line segment(s) in a second ultrasound image using a Hough transform algorithm according to some embodiments of the present disclosure. In some embodiments, the process 400 may be performed to achieve at least part of operation 304 as described in connection with FIG. 3.

It should be noted that the descriptions of the Hough transform algorithm are provided for the purposes of illustration, and are not intended to limit the scope of the present disclosure. For example, the line segment(s) in the second ultrasound image can be identified using a region growing algorithm, a machine learning algorithm, etc.

In 402, the processing device 140 (e.g., the identification module 220) may generate a binary image by performing a binary operation on at least a portion of a second ultrasound image.

The portion of the second ultrasound image refers to an image region in the second ultrasound image including a linear interventional device (e.g., the linear interventional device 104). For example, the portion of the second ultrasound image may be an image region in the second ultrasound image including a representation of the linear interventional device.

In some embodiments, the processing device 140 may generate the portion of the second ultrasound image by segmenting the representation of the linear interventional device from the second ultrasound image of the target subject. For example, the processing device 140 may segment the representation of the linear interventional device from the ultrasound medical image based on an image segmentation technique. Exemplary image segmentation techniques may include a region-based segmentation, an edge-based segmentation, a wavelet transform segmentation, a mathematical morphology segmentation, a genetic algorithm-based segmentation, a machine learning-based segmentation, or the like, or any combination thereof. As another example, the processing device 140 may select the representation of the linear interventional device from the second ultrasound image using a selection box. The selection box (also referred to as a first selection box) may have a certain shape, such as a rectangle, a circle, an ellipse, an irregular polygon, etc. A size of the selection box may be smaller than the size of the second ultrasound image. In some embodiments, the shape and/or size of the selection box may be determined based on a system default setting or set manually by a user (e.g., a technician, a doctor, a physicist, etc.). By determining the portion of the second ultrasound image, subsequent operation(s) (e.g., the binary operation) only need to be performed on the portion of the second ultrasound image other than the whole second ultrasound image, which can reduce a processing amount and improve the efficiency of the line detection. In addition, interferences of other lines in the second ultrasound image can be reduced, which can improve the accuracy of the line detection.

Figure 8A:
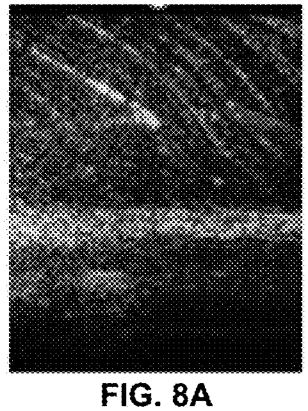
FIG. 8A is a schematic diagram illustrating an exemplary first ultrasound image according to some embodiments of the present disclosure example.
Figure 8B:
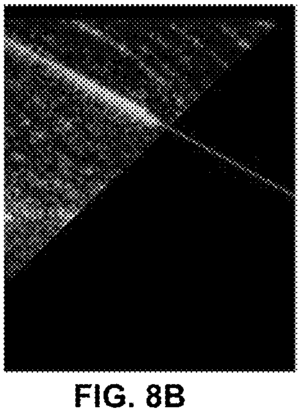
FIG. 8B is a schematic diagram illustrating an exemplary second ultrasound image according to some embodiments of the present disclosure example.
Figure 8C:
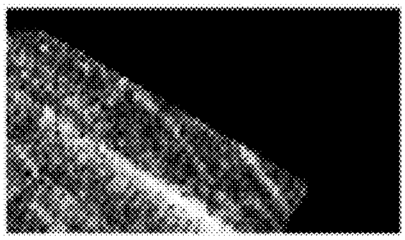
FIG. 8C is a schematic diagram illustrating at least a portion of the second ultrasound image including a linear interventional device as shown in FIG. 8B.
Figure 8D:
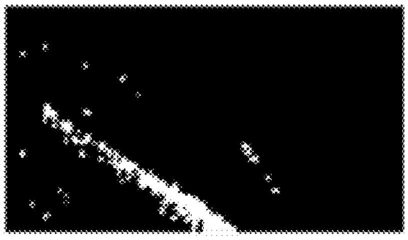
FIG. 8D is a schematic diagram illustrating a binary image of the portion of the second ultrasound image as shown in FIG. 8C.

In some embodiments, the processing device 140 may generate the binary image by performing the binary operation on the portion of the second ultrasound image. The binary operation refers to an operation that sets a gray value of each pixel point in an image to 0 or 1, and the binary image refers to an image whose gray value of each pixel point in the image is 0 or 1. Therefore, the binary image presents an obvious black and white effect, which can improve the contrast between the background and the representation of the linear interventional device. For example, as illustrated in FIG. 8D, a white portion of a binary image 820 is the representation of the linear interventional device, and a black portion of the binary image 820 is the background.

In some embodiments, the processing device 140 may perform the binary operation on the portion of the second ultrasound image using an algorithm, such as an Otsu algorithm, an adaptive threshold segmentation algorithm, a global threshold algorithm, a local threshold algorithm, a P-quantile algorithm, an iterative algorithm, an entropy algorithm, etc. The adaptive threshold segmentation algorithm is used to divide the portion of the second ultrasound image into a first part of the background and a second part of the linear interventional device based on grayscale characteristics of the portion of the second ultrasound image. Through the adaptive threshold segmentation algorithm, a definition of the linear interventional device in the binary image can be improved, which improves the accuracy of the line detection. By performing the binary operation on the portion of the second ultrasound image, the binary image can be generated, which reduces the processing amount of the line detection and highlights the representation of the linear interventional device in the portion of the second ultrasound image, thereby improving the efficiency and accuracy of the line detection.

In 404, the processing device 140 (e.g., the identification module 220) may obtain one or more lines by processing the binary image using the Hough transform algorithm.

A line (also referred to as a target line) refers to a line where the representation of the linear interventional device is possible to locate in the second ultrasound image. For example, the target line may include a line segment indicating a candidate representation of the linear interventional device in the second ultrasound image.

Since the Hough transform algorithm can be used to identify features (e.g., lines) in images, the processing device 140 may obtain the one or more lines by processing the binary image using the Hough transform algorithm.

Merely by way of example, the processing device 140 may obtain multiple parametric curves in the Hough parameter space by performing the Hough transform on the binary image. The Hough transform can fit a line or a curve by transforming an image coordinate system into a parameter coordinate system (also referred to as the Hough parameter space). The Hough parameter space may include a linear parameter coordinate space, a polar parameter coordinate space, etc. For example, a line in the binary image may be represented as a first equation $y=kx+b$ or a second equation $\rho=x \cos \theta+y \sin \theta$, and a parameter coordinate (k, b) or ($\rho$, $\theta$) may uniquely represent the line. The parameter coordinate (k, b) or ($\rho$, $\theta$) of each line in the binary image may form the Hough parameter space. That is, the linear parameter coordinate space is established using k as a horizontal axis and b as a vertical axis. Alternatively, the polar parameter coordinate space is established using $\rho$ as a horizontal axis and $\theta$ as a vertical axis. Correspondingly, each point in the binary image can be represented as a line or a curve in the Hough parameter space. For example, a point (p,q) in the binary image can be represented as a third equation $b=-kp+q$ in the linear parameter coordinate space. For instance, the processing device 140 may determine multiple pixel points each of whose gray value is equal to 1, and generate the multiple parametric curves in the Hough parameter space based on coordinates of the multiple pixel points in the image coordinate system.

In some embodiments, the processing device 140 may determine at least one intersection point of the plurality of parametric curves in the Hough parameter space. For example, when some pixel points in the binary image are collinear, parameter curves corresponding to the some pixel points may intersect at a same intersection point in the Hough parameter space, and a parameter coordinate corresponding to the intersection point may be the line in the binary image where the some pixel points are located. In some embodiments, for each intersection point in the Hough parameter space, the processing device 140 may determine a count of parametric curves intersected at the intersection point. For example, if an intersection point $P_L$ is crossed by M parameter curves, the processing device 140 may determine the count of parametric curves intersecting at the intersection point $P_L$ as M. Further, the processing device 140 may determine the one or more lines based on the count of parametric curves corresponding to each intersection point. For example, the processing device 140 may determine an intersection point with a maximum count as a target point, and determine a line in the binary image corresponding to the target point as the one or more lines. As another example, the processing device 140 may determine a count threshold (e.g., 3, 4, 5, etc.), determine intersection point(s) each of whose count of parametric curves is larger than or equal to the count threshold as target point(s), and determine line(s) in the binary image corresponding to the target point(s) as the one or more target lines. In some embodiments, the count threshold may be determined based on a system default setting or set manually by a user. By determining the target point(s) with a count of parametric curves larger than or equal to the count threshold, the one or more target lines with a relatively high possibility where the representation of the linear interventional device is located can be determined in the binary image, which improves the accuracy of the line detection.

In 406, for each of the one or more lines, the processing device 140 (e.g., the identification module 220) may determine, in the binary image, a plurality of pixel points that correspond to the linear interventional device and are located on the line.

For example, for each of the one or more lines, the processing device 140 may determine pixel points that are on the line and have gray value of 1.

In 408, for each of the one or more lines, the processing device 140 (e.g., the identification module 220) may determine a line segment corresponding to the line based on the plurality of pixel points.

For example, for each of the one or more lines, the processing device 140 may generate candidate line segments by connecting each two pixel points among the plurality of pixel points corresponding to the line, and determine a length of each of the candidate line segments. The processing device 140 may further determine a candidate line segment with a maximum length as the line segment corresponding to the line. The line segment may be represented by coordinates of two endpoints. As another example, for each of the one or more lines, the processing device 140 may determine two pixel points having the largest distance from each other among the pixel points of the line, and determine the line segment based on the two pixel points, wherein the two pixel points may be two endpoints of the line segment.

According to some embodiments of the present disclosure, by determining the line segment(s) using the Hough transform algorithm, a position of the linear interventional device can be coarsely determined, which can be used in subsequent processing, thereby reducing the processing amount of the subsequent processing and improving the efficiency of the line detection. In addition, the Hough transform algorithm has a high sensitivity, and the line segment(s) can be identified with high efficiency using a little time.

Figure 5:
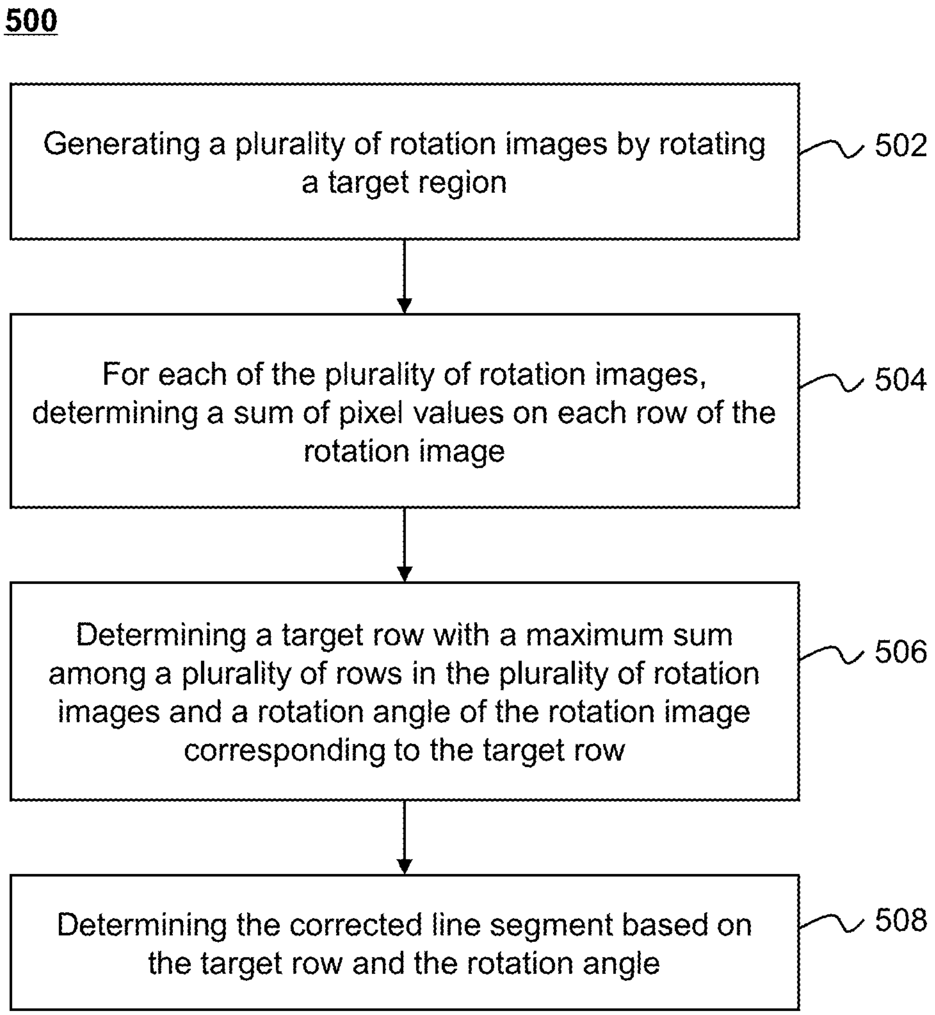
FIG. 5 is a flowchart illustrating an exemplary process for determining a corrected line segment for a line segment according to some embodiments of the present disclosure.

FIG. 5 is a flowchart illustrating an exemplary process 500 for determining a corrected line segment for a line segment according to some embodiments of the present disclosure. In some embodiments, the process 500 may be performed to achieve at least part of operation 306 as described in connection with FIG. 3. In some embodiments, the process 500 may be performed for each of the one or more line segment determined in operation 304 to determine the corresponding corrected line segment.

In 502, the processing device 140 (e.g., the determination module 230) may generate a plurality of rotation images by rotating a target region corresponding to the line segment.

The target region refers to an image region in a second ultrasound image where the line segment is located. For example, the processing device 140 may determine the target region based on coordinates of the two endpoints of the line segment. As another example, the processing device 140 may select the line segment from the ultrasound medical image using a second selection box to generate the target region. The second selection box may be similar to the first selection box as described above. For example, the second selection box may be a rectangle box enclosing the line segment. By determining one or more target regions corresponding to the line segment(s), subsequent operation(s) only need to be performed on the one or more target regions other than the whole second ultrasound image, which can reduce a processing amount and improve the efficiency of the line detection.

In some embodiments, for each of line segment(s), the processing device 140 may rotate the target region corresponding to the line segment based on an angle step (e.g., 0.1 degrees, 0.2 degrees, 0.5 degrees, 0.8 degrees, 1.0 degrees, 1.2 degrees, 1.5 degrees, 2.0 degrees, 5.0 degrees, 10 degrees, etc.) in a preset angle range (e.g., 0 to 180 degrees, 0 to 90 degrees, 0 to 60 degrees, 0 to 30 degrees, −30 to 30 degrees, −10 to 10 degrees, −3 to 3 degrees, etc.). For example, if the angle step is 0.1 degrees, and the preset angle range is the angle range from −3 to 3 degrees, the processing device 140 may rotate the target region 60 times (i.e., by −3 degrees, . . . , −0.1 degrees, 0.1 degrees, . . . , 3 degrees) to obtain 60 rotation images. In some embodiments, the angle step and/or the preset angle range may be determined based on a system default setting or set manually by a user (e.g., a technician, a doctor, a physicist, etc.).

In some embodiments, before rotating the target region corresponding to the line segment, the processing device 140 may post-process the target region. For example, the processing device 140 may obtain a filtered image by filtering the target region using a Gabor filtering algorithm, and generate the plurality of rotation images by rotating the filtered image. By using the Gabor filtering algorithm, the target region can be filtered, which reduces noise(s) in the target region, thereby improving the accuracy of the line detection. As another example, the processing device 140 may obtain an equalized image by performing a histogram equalization on the target region, and generate the plurality of rotation images by rotating the equalized image. The histogram equalization may be used to adjust a contrast of the target region by using a gray histogram of the target region or the second ultrasound image. Through the histogram equalization, the brightness of the target region can be improved, which can enhance a local contrast without affecting the overall contrast, thereby improving the accuracy of the line detection.

In 504, for each of the plurality of rotation images, the processing device 140 (e.g., the determination module 230) may determine a sum of pixel values on each row of the rotation image.

A row may include pixel points in a horizontal line of a rotation image, and the horizontal line is parallel to a horizontal direction of the second ultrasound image.

In some embodiments, for each of the plurality of rotation images, the processing device 140 may determine pixel points whose pixel values need to be summed. For example, the processing device 140 may determine a sum region based on coordinates of two endpoints corresponding to the line segment and a rotation angle. For instance, the processing device 140 may determine rotated coordinates of the two endpoints based on the coordinates of the two endpoints and the rotation angle, and determine a rotated line segment (e.g., an equation of the rotated line segment) based on the rotated coordinates of the two endpoints. The processing device 140 may further determine the pixel points on the rotated line segment, and the pixel values of whose pixel points need to be summed. By determining the pixel points whose pixel values need to be summed, a processing amount can be reduced, which can improve the efficiency of the line detection. In addition, interferences of other pixel values in the rotation image can be reduced, which can improve the accuracy of the line detection.

In some embodiments, the processing device 140 may determine the sum of pixel values on each row of the rotation image based on the pixel points whose pixel values need to be summed in the row.

In 506, the processing device 140 (e.g., the determination module 230) may determine a target row with a maximum sum among a plurality of rows in the plurality of rotation images and a rotation angle of the rotation image corresponding to the target row. The plurality of rotation images may correspond to a same line segment.

For example, the processing device 140 may compare sums of the plurality of rows in the plurality of rotation images to determine the maximum sum, and designate a row with the maximum sum as the target row corresponding to the line segment.

In some embodiments, the processing device 140 may perform a normalization operation on each of the plurality of rows in the plurality of rotation images. For example, the processing device 140 may obtain a normalized sum of each of the plurality of rows by dividing the sum of the row by a length of the corresponding line segment. The length of the line segment refers to a geometric distance of the line segment. For example, the length of the line segment may be a distance between two endpoints corresponding to the line segment that is determined based on coordinates of the two endpoints. Further, the processing device 140 may determine the target row with a maximum normalized sum among the plurality of rows in the plurality of rotation images and the rotation angle of the rotation image corresponding to the target row. For brevity, the rotation angle corresponding to the target row is referred to as the target rotation angle, and the rotation image corresponding to the target rotation angle is referred to as the target rotation image. By performing the normalization operation, the effect of the lengths of the corrected line segments can be eliminated the detection accuracy of short lines using the Radon transform algorithm can be improved.

In 508, the processing device 140 (e.g., the determination module 230) may determine a corrected line segment based on the target row and the rotation angle (the target rotation angle).

In some embodiments, based on the position of the target row in the target rotation image and the target rotation angle, the processing device 140 may determine the position of a second target row in the second ultrasound image corresponding to the target row. A line located at the target row in the second ultrasound image may be determined as a corrected line. The processing device 140 may further determine a line segment corresponding to the corrected line as the corrected line segment. The determination of the line segment corresponding to the corrected line may be performed in a similar manner as that of the line segment corresponding to a line as described in connection with FIG. 4. For example, the processing device 140 may determine two pixel points on the corrected line that have the longest distance from each other, and designate the two pixel points as the endpoints of the corrected line segment.

By using the second line detection algorithm, corrected line segment(s) corresponding to the line segment(s) can be determined. Since the second line detection algorithm has a high precision, the accuracy of the line detection can be improved.

It should be noted that the descriptions are provided for the purposes of illustration, and are not intended to limit the scope of the present disclosure. For persons having ordinary skills in the art, various variations and modifications may be conducted under the teaching of the present disclosure. For example, the corrected line segment may be determined using other manners. For instance, the corrected line segment may be determined based on lines besides the row of the rotation image, such as, a column in a vertical line of the rotation image, a line with a certain included angle with respect to the row, etc. Merely by way of example, the processing device 140 may generate a plurality of rotation images by rotating a target region corresponding to the line segment. For each of the plurality of rotation images, the processing device 140 may determine a sum of pixel values on each column of the rotation image. A column may include pixel points in a vertical line of a rotation image, and the vertical line is parallel to a vertical direction of the second ultrasound image. The processing device 140 may determine a target column with a maximum sum among a plurality of columns in the plurality of rotation images and a rotation angle of the rotation image corresponding to the target column. The plurality of rotation images may correspond to a same line segment. Further, the processing device 140 may determine the corrected line segment based on the target column and the rotation angle (the target rotation angle).

As another example, the processing device 140 may determine the target region corresponding to the line segment, and determine lines of the target region corresponding to a plurality of directions. For each of the plurality of directions, the lines corresponding to the direction may form the target region, and the lines may be parallel to the direction. Each direction of the plurality of directions refers to a direction that has an angle with respect to a certain direction (e.g., a vertical direction, a horizontal direction, etc.) of the second ultrasound image. For each of the plurality of directions, the processing device 140 may determine a sum of pixel values on each line of the target region. The processing device 140 may determine a target line with a maximum sum among a plurality of lines corresponding to the plurality of directions and a target angle corresponding to the target line, and determine the corrected line segment based on the target line and the target angle.

Figure 6:
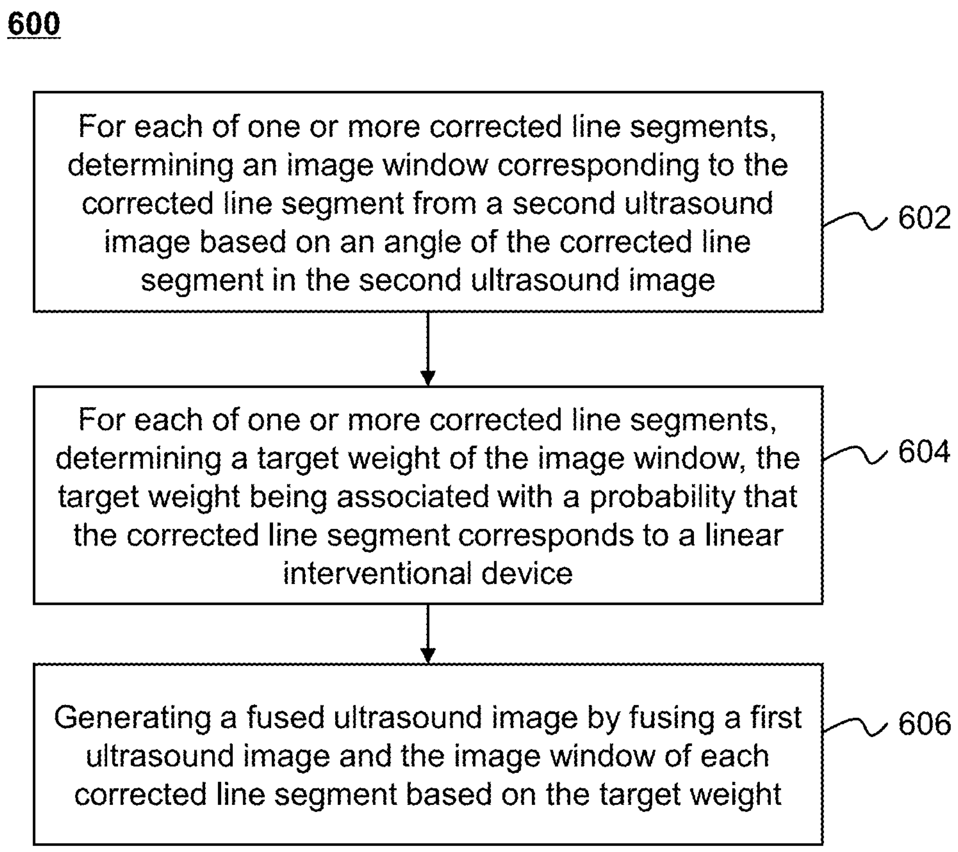
FIG. 6 is a flowchart illustrating an exemplary process for generating a fused ultrasound image according to some embodiments of the present disclosure.

FIG. 6 is a flowchart illustrating an exemplary process 600 for generating a fused ultrasound image according to some embodiments of the present disclosure. In some embodiments, the process 600 may be performed to achieve at least part of operation 308 as described in connection with FIG. 3.

In 602, for each of corrected line segment(s), the processing device 140 (e.g., the generation module 240) may determine an image window corresponding to a corrected line segment from a second ultrasound image based on an angle of the corrected line segment in the second ultrasound image.

The angle of the corrected line segment refers to an inclination angle of the corrected line segment in the second ultrasound image. For example, the angle of the corrected line segment may be an included angle between the corrected line segment and an edge (e.g., a long edge, a short edge, etc.) of the second ultrasound image.

The image window refers to an image region including the corrected line segment in the second ultrasound image. For example, the corrected line segment may be located in the middle of two length edges of the image window and be parallel to the length edges.

In some embodiments, for each of corrected line segment(s), the processing device 140 may obtain a preset width of the image window, and determine a length of the image window based on the preset width and the angle of the corrected line segment. For example, the length of the image window may be a value obtained by dividing the preset width by a cosine value of the angle of the corrected line segment. The processing device 140 may further determine the image window corresponding to the corrected line segment based on the preset width and the length of the image window. In some embodiments, the preset width may be determined based on a system default setting or set manually by a user (e.g., a technician, a doctor, a physicist, etc.).

In 604, for each of the corrected line segment(s), the processing device 140 (e.g., the generation module 240) may determine a target weight of the image window corresponding to the corrected line segment. The target weight may be associated with a probability that the corrected line segment corresponds to a linear interventional device.

In some embodiments, for each of the corrected line segment(s), the processing device 140 may perform the following operations. The processing device 140 may obtain an initial weight of the image window. For example, the processing device 140 may designate a maximum normalized sum corresponding to a target row of the corrected line segment as the initial weight. The processing device 140 may further determine a plurality of vertical lines on the corrected line segment corresponding to the image window. A count of the plurality of vertical lines may be determined based on a system default setting or set manually by a user (e.g., a technician, a doctor, a physicist, etc.). In some embodiments, each of the plurality of vertical lines may cross the corrected line segment, and lengths of the plurality of vertical lines may be the same or different.

For each of the plurality of vertical lines, the processing device 140 may determine a plurality of pixel points in the second ultrasound image on the vertical line, and obtain pixel values of the plurality of pixel points on the vertical line. Further, the processing device 140 may determine whether the pixel values of the plurality of pixel points on each of the plurality of vertical lines satisfy a first preset condition. For example, the processing device 140 may determine an average value of each of the plurality of vertical lines based on the pixel values of the plurality of pixel points on the vertical line, and then the processing device 140 may determine multiple maximum values among a plurality of average values corresponding to the plurality of vertical lines. For instance, the processing device 140 may generate a curve, wherein the horizontal axis represents the position of the vertical lines, and the vertical axis represents the average value corresponding to each vertical line. The peaks in the curve are the maximum values. The processing device 140 may determine whether the vertical lines corresponding to the maximum values (i.e., the peaks) are equally spaced. If the vertical lines corresponding to the maximum values (i.e., the peaks) are equally spaced, the first preset condition may be satisfied.

If the first preset condition is satisfied, it may indicate that the corrected line segment has artifact segments with equal spacing and multiple extreme values, and the probability that the corrected line segment corresponds to the linear interventional device is relatively high. The artifact is probably caused by a phenomenon that an echo signal displayed by an ultrasound imaging device is inconsistent with an actual position of a detected echo interface due to the physical effect of the ultrasonic propagation during the process of ultrasonic imaging, parameters (e.g., an amplitude, a gray level, etc.) of the echo signal displayed are inconsistent with the characteristics of the echo interface, etc. The artifacts in ultrasound images include multiple reflections, refraction, sidelobe artifacts, grating lobe artifacts, or the like, or any combination thereof. If the first preset condition is satisfied, the processing device 140 may determine the target weight of the image window based on the initial weight of the image window and a preset coefficient. For example, the processing device 140 may determine the target weight of the image window by multiplying the initial weight of the image window and the preset coefficient. The preset coefficient may be greater than 1, which may be determined based on a system default setting or set manually by a user.

If the first preset condition is not satisfied, it may indicate that the probability that the corrected line segment corresponds to the linear interventional device is relatively low. Correspondingly, the processing device 140 may determine the initial weight as the target weight, or the processing device 140 may determine the target weight of the image window by multiplying the initial weight of the image window and a second preset coefficient. The second preset coefficient may be a relatively little value (e.g., 0, 0.1, 0.2, etc.), which may be determined based on a system default setting or set manually by a user.

In some embodiments, the processing device 140 may determine the probability that the corrected line segment corresponds to the linear interventional device through other manners, such as a brightness analysis, a gray-scale analysis, etc., and determine the target weight of the image window based on the probability that the corrected line segment corresponds to the linear interventional device and the initial weight of the image window.

In 606, the processing device 140 (e.g., the generation module 240) may generate a fused ultrasound image by fusing the first ultrasound image and the image window of each corrected line segment based on the target weight.

In some embodiments, for each corrected line segment, the processing device 140 may determine a sub-weight of each pixel point in the image window corresponding to the corrected line segment based on the target weight of the image window. For example, a sub-weight of a pixel point near a center of the image window may be larger than a sub-weight of a pixel point near an edge of the image window. For instance, the sub-weight of each pixel point in the image window may be determined by multiplying the target weight of the image window by a weight coefficient, wherein the weight coefficient corresponding to the pixel point near the center of the image window is the largest, and a weight coefficient corresponding to the pixel point near the edge of the image window is the smallest. As another example, the processing device 140 may determine the sub-weight of each pixel point in the image window based on a weight function, such as a linear descent function, a multi-segment curve descent function, a log type descent function, etc., wherein a distance between each pixel point and the center of the image window is taken as a horizontal coordinate of the weight function, and the sub-weight of each pixel point is taken as a vertical coordinate of the weight function.

As another example, the processing device 140 may directly designate the target weight of the image window as the sub-weight of each pixel point in the image window.

The processing device 140 may further determine a weighted image window by processing each pixel point in the image window based on the sub-weight of each pixel point. For example, the processing device 140 may obtain a weighted pixel value of each pixel point in the image window by weighting the pixel value of each pixel point based on the sub-weight of each pixel point, and then determine the weighted image window based on the weighted pixel value of each pixel point in the image window.

Then, the processing device 140 may generate the fused ultrasound image by fusing the first ultrasound image and the weighted image window of each corrected line segment. For example, the processing device 140 may fuse the first ultrasound image and the weighted image window of each corrected line segment according to an image fusion algorithm, such as, a weighted fusion algorithm, a grayscale-based fusion algorithm, a pyramid fusion algorithm, a gradient domain fusion algorithm, a wavelet transform algorithm, a structural deformation algorithm, etc.

By fusing the first ultrasound image and the weighted image window of each corrected line segment, instead of fusing the first ultrasound image with the whole second ultrasound image, the processing amount can be reduced and the efficiency of the image fusion can be improved. In addition, each weighted image window is determined based on the target weight of the image window which relates to the probability that the corrected line segment corresponds to the linear interventional device, which can reduce the effect of other lines on the image fusion, thereby the accuracy of the image fusion. Besides, interferences in other portions of the second ultrasound image other than the target region(s) cannot affect the image fusion, which can improve the accuracy of the image fusion, thereby improving the accuracy and efficiency of the determination (e.g., positioning) of the linear interventional device.

Figure 7:
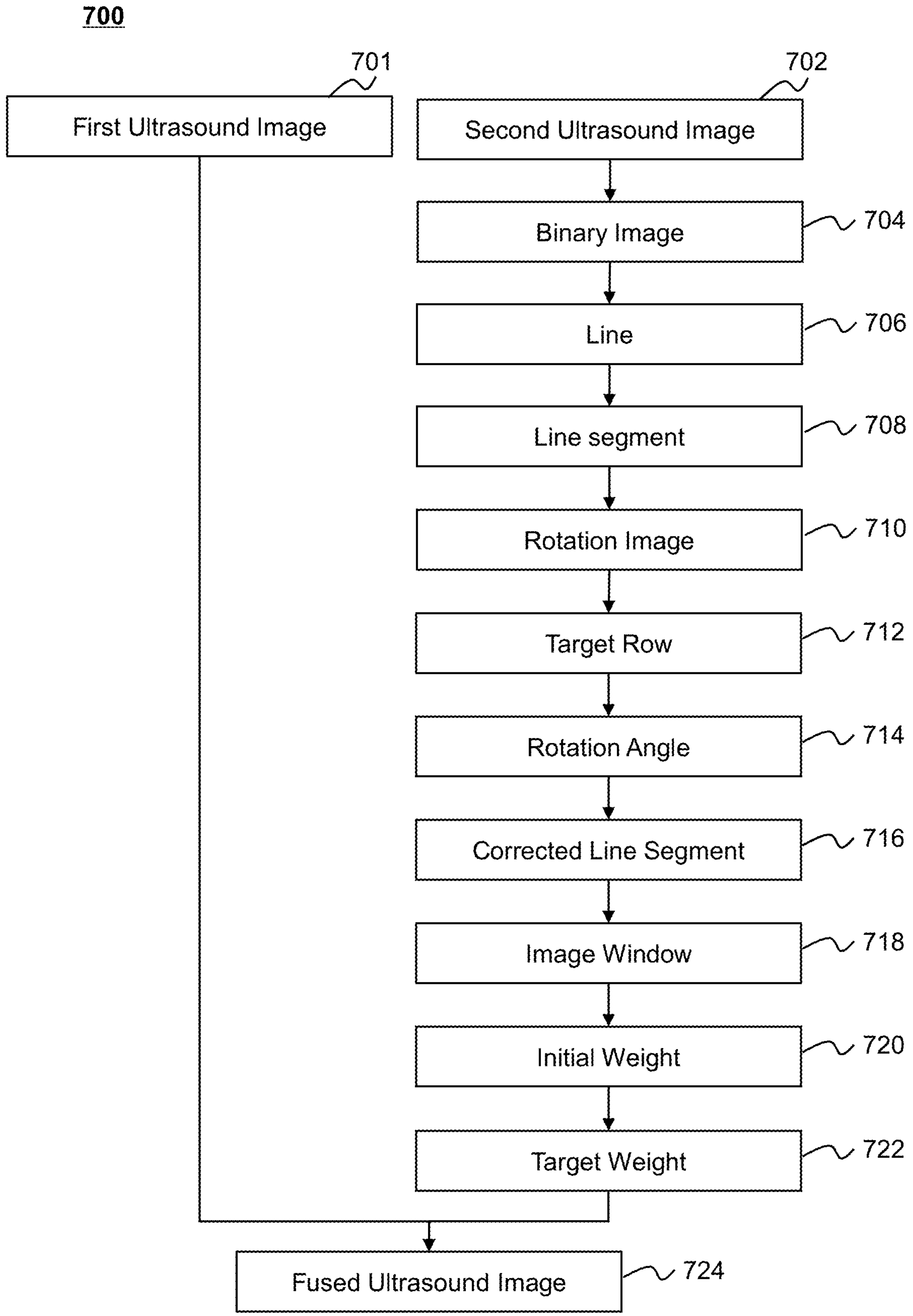
FIG. 7 is a flowchart illustrating an exemplary process for generating a fused ultrasound image according to some embodiments of the present disclosure.

FIG. 7 is a schematic diagram illustrating an exemplary process 700 for image processing according to some embodiments of the present disclosure.

A first ultrasound image 701 and a second ultrasound image 702 of a target subject may be obtained. The first ultrasound image 701 and the second ultrasound image 702 may include a linear interventional device within the target subject. The first ultrasound image 701 may be captured by emitting ultrasonic waves toward the target subject along a first angle with respect to an insertion direction of the linear interventional device, the second ultrasound image 702 may be captured by emitting ultrasonic waves toward the target subject along a second angle with respect to an insertion direction of the linear interventional device, and the second angle may be closer to 90 degrees than the first angle. The linear interventional device may be still between a time period when the first ultrasound image 701 and the second ultrasound image 702 are captured. Referring to FIGS. 8A and 8B, FIG. 8A is a schematic diagram illustrating an exemplary first ultrasound image 802 according to some embodiments of the present disclosure example, and FIG. 8B is a schematic diagram illustrating an exemplary second ultrasound image 804 according to some embodiments of the present disclosure example. The linear interventional device in the second ultrasound image 804 has a higher image resolution than that in the first ultrasound image 802.

Referring back to FIG. 7, A binary image 704 may be generated by performing a binary operation on at least a portion of the second ultrasound image 702. Referring to FIGS. 8C and 8D, FIG. 8C is a schematic diagram illustrating a portion 810 of the second ultrasound image 804 including the linear interventional device, FIG. 8D is a schematic diagram illustrating a binary image 820 of the portion 810. For example, the portion 810 of the second ultrasound image 804 may be segmented from the second ultrasound image 804, and the binary image 820 may be generated by performing a binary operation on the portion 810 of the second ultrasound image 804.

Figure 8E:
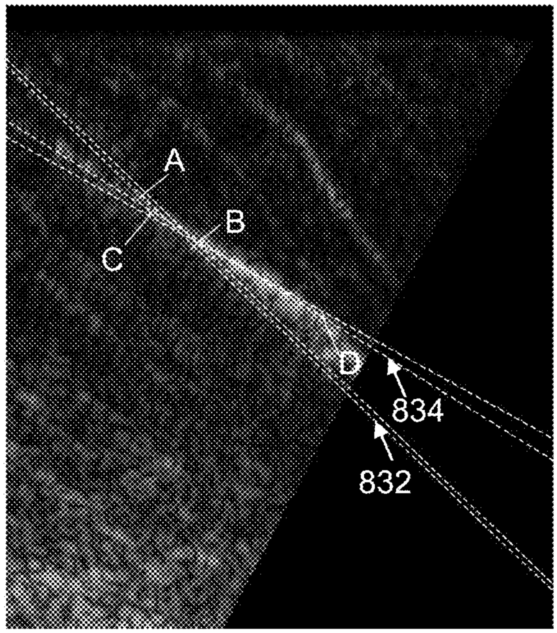
FIG. 8E is a schematic diagram illustrating an exemplary second ultrasound image processed using a Hough transform algorithm according to some embodiments of the present disclosure example.

One or more lines 706 may be obtained by processing the binary image 704 using a Hough transform algorithm. For each of the one or more lines 706, a plurality of pixel points that correspond to the linear interventional device and are located on the line may be determined, and a line segment 708 corresponding to the line based on the plurality of pixel points may be determined. Referring to FIG. 8E, FIG. 8E is a schematic diagram illustrating an exemplary second ultrasound image 804 processed using a Hough transform algorithm according to some embodiments of the present disclosure example. As illustrated in FIG. 8E, pixel points A and B are located on a line 832, and form a line segment AB. Pixel points C and D are located on a line 834, and form a line segment CD.

Figure 8F:
FIG. 8F is a schematic diagram illustrating an exemplary rotation image according to some embodiments of the present disclosure example.

For each of the line segment(s) 708, a target region in the second ultrasound image 702 corresponding to the line segment 708 may be determined, and a plurality of rotation images 710 may be generated by rotating the target region. Referring to FIG. 8F, FIG. 8F is a schematic diagram illustrating an exemplary rotation image 840 according to some embodiments of the present disclosure example.

For each of the plurality of rotation images 710, a sum of pixel values on each row of the rotation image 710 may be determined, and a target row 712 with a maximum sum among a plurality of rows in the plurality of rotation images 710 may be determined. Further, for each of the plurality of rotation images 710, a rotation angle 714 of the rotation image 710 corresponding to the target row 712 may be determined.

Figure 8G:
FIG. 8G is a schematic diagram illustrating an exemplary image window according to some embodiments of the present disclosure example.

For each of the line segment(s) 708, a corrected line segment 716 may be determined based on the target row 712 and the rotation angle 714. An image window 718 corresponding to the corrected line segment 716 may be determined from the second ultrasound image 702 based on an angle of the corrected line segment 716 in the second ultrasound image 702. Referring to FIG. 8G, FIG. 8G is a schematic diagram illustrating an exemplary image window 850 according to some embodiments of the present disclosure example.

An initial weight 720 of the image window 718 may be determined, and a target weight 722 of the image window 718 may be determined based on the initial weight 720.

Figure 8H:
FIG. 8H is a schematic diagram illustrating an exemplary fused ultrasound image according to some embodiments of the present disclosure example.

A fused ultrasound image 724 may be generated by fusing the first ultrasound image 701 and the image window 718 of each corrected line segment based on the target weight 722. Referring to FIG. 8H, FIG. 8H is a schematic diagram illustrating an exemplary fused ultrasound image 860 according to some embodiments of the present disclosure example. The fused ultrasound image 860 has a better imaging quality with respect to the linear interventional device than the first ultrasound image 802.

Figure 9A:
FIG. 9A is a schematic diagram illustrating an exemplary first ultrasound image according to some embodiments of the present disclosure example.
Figure 9B:
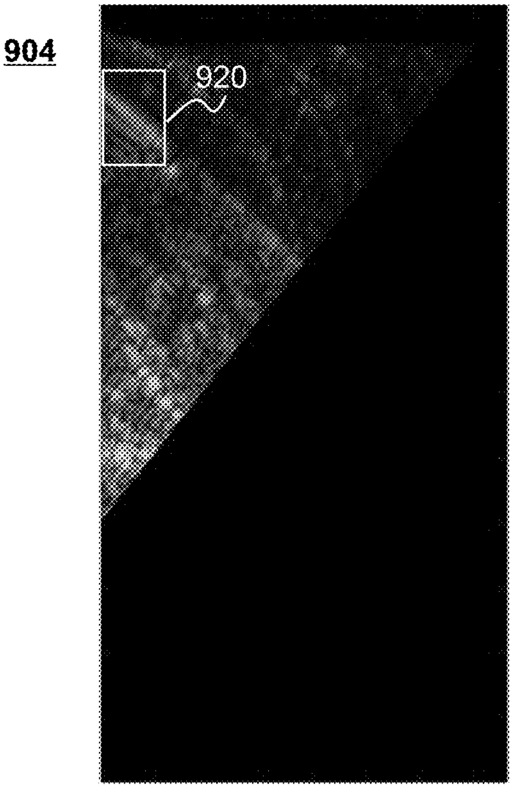
FIG. 9B is a schematic diagram illustrating an exemplary second ultrasound image according to some embodiments of the present disclosure example.
Figure 9C:
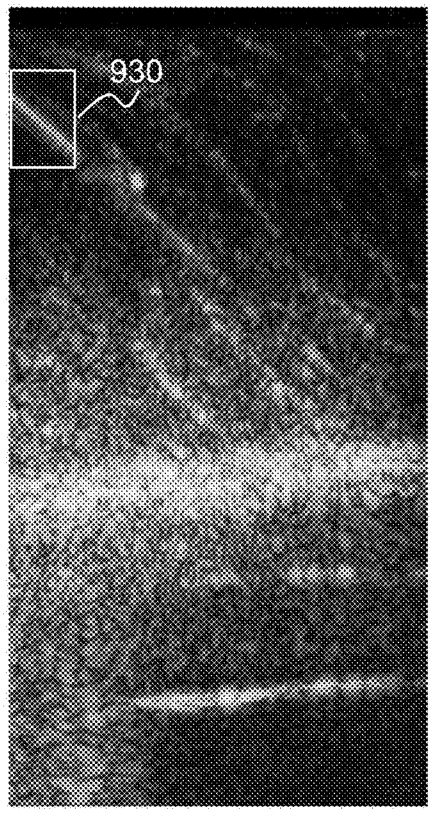
FIG. 9C is a schematic diagram illustrating an exemplary fused ultrasound image according to some embodiments of the present disclosure example.

In some embodiments, the process 700 may be used to process ultrasound images with artifacts. Referring to FIGS. 9A-9C, FIG. 9A is a schematic diagram illustrating an exemplary first ultrasound image 902 according to some embodiments of the present disclosure example, FIG. 9B is a schematic diagram illustrating an exemplary second ultrasound image 904 according to some embodiments of the present disclosure example, and FIG. 9C is a schematic diagram illustrating an exemplary fused ultrasound image 906 according to some embodiments of the present disclosure example. As illustrated in FIGS. 9A-9C, the fused ultrasound image 906 is generated by fusing the first ultrasound image 902 and the second ultrasound image 904 according to the first line detection algorithm and the second line detection algorithm. A region 910 in the first ultrasound image 902 includes no representation of the linear interventional device, and a region 920 in the second ultrasound image 904 and a region 930 in the fused ultrasound image 906 include the representation of the linear interventional device. The fused ultrasound image 906 has a relatively high image quality without being affected by the artifacts in the first ultrasound image 902 and the second ultrasound image 904.

It should be noted that the descriptions of the processes 300-700 are provided for the purposes of illustration, and are not intended to limit the scope of the present disclosure. For persons having ordinary skills in the art, various variations and modifications may be conducted under the teaching of the present disclosure. For example, the processes 300-700 may be accomplished with one or more additional operations not described, and/or without one or more of the operations discussed. Additionally, the order in which the operations of the processes 300-700 is not intended to be limiting. However, those variations and modifications may not depart from the protection of the present disclosure.

Figure 10:
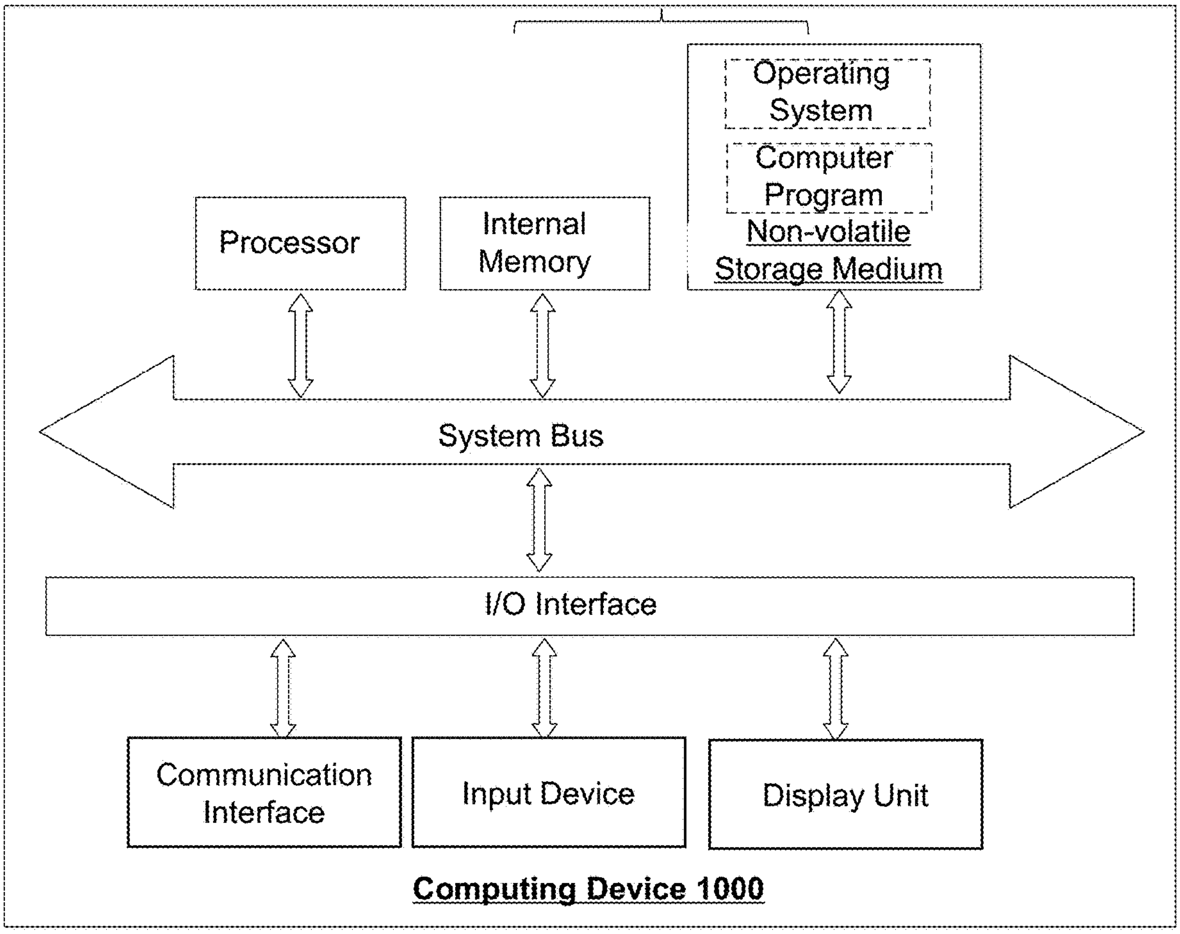
FIG. 10 is a schematic diagram illustrating an exemplary computing device according to some embodiments of the present disclosure.

FIG. 10 is a schematic diagram illustrating an exemplary computing device 1000 according to some embodiments of the present disclosure.

In some embodiments, one or more components of the image processing system 100 may be implemented on the computing device 1000. For example, a processing engine may be implemented on the computing device 1000 and configured to implement the functions and/or methods disclosed in the present disclosure.

The computing device 1000 may include any components used to implement the image processing system 100 described in the present disclosure. For example, the processing device 140 may be implemented through hardware, software program, firmware, or any combination thereof, on the computing device 1000. For illustration purposes, only one computer is described in FIG. 10, but computing functions related to the image processing system 100 described in the present disclosure may be implemented in a distributed fashion by a group of similar platforms to spread the processing load of the image processing system 100.

The computing device 1000 may include a communication port connected to a network to achieve data communication. The computing device 1000 may include a processor (e.g., a central processing unit (CPU)), a memory, a communication interface, a display unit, and an input device connected by a system bus. The processor of the computing device 1000 may be used to provide computing and control capabilities. The memory of the computing device 1000 may include a non-volatile storage medium, an internal memory. The non-volatile storage medium may store an operating system and a computer program. The internal memory may provide an environment for the execution of the operating system and the computer program in the non-volatile storage medium. The communication interface of the computing device 1000 may be used for wired or wireless communication with an external terminal. The wireless communication may be realized through Wi-Fi, a mobile cellular network, a near field communication (NFC), etc. When the computer program is executed by the processor, a method for determining feature points may be implemented. The display unit of the computing device 1000 may include a liquid crystal display screen or an electronic ink display screen. The input device of the computing device 1000 may include a touch layer covered on the display unit, a device (e.g., a button, a trackball, a touchpad, etc.) set on the housing of the computing device 1000, an external keyboard, an external trackpad, an external mouse, etc.

Merely for illustration, only one processor is described in FIG. 10. However, it should be noted that the computing device 1000 in the present disclosure may also include multiple processors. Thus operations and/or method steps that are performed by one processor as described in the present disclosure may also be jointly or separately performed by the multiple processors. For example, if the processor of the computing device 1000 in the present disclosure executes both operation A and operation B, it should be understood that operation A and operation B may also be performed by two or more different processors jointly or separately (e.g., a first processor executes operation A and a second processor executes operation B, or the first and second processors jointly execute operations A and B).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for ultrasound image processing, implemented on a computing device having at least one processor and at least one storage device, the method comprising:

obtaining a first ultrasound image and a second ultrasound image of a target subject, the first ultrasound image and the second ultrasound image including a linear interventional device within the target subject, the first ultrasound image and the second ultrasound image being captured by emitting different ultrasonic waves toward the target subject, and the second ultrasound image having a better imaging quality with respect to the linear interventional device than the first ultrasound image;

identifying one or more line segments in the second ultrasound image by processing the second ultrasound image using a first line detection algorithm, wherein the first line detection algorithm is a Hough transform algorithm;

for each of the one or more line segments, determining a target region in the second ultrasound image corresponding to the line segment, wherein the target region is a local image region in the second ultrasound image including the line segment;

determining a corrected line segment by processing the target region in the second ultrasound image corresponding to the line segment using a second line detection algorithm, wherein the second line detection algorithm is a Radon transform algorithm, and a detection precision of the second line detection algorithm is higher than a detection precision of the first line detection algorithm; and generating a fused ultrasound image of the first ultrasound image and the second ultrasound image based on one or more corrected line segments corresponding to the one or more line segments.

2. The method of claim 1, wherein the first ultrasound image is captured by emitting ultrasonic waves toward the target subject along a first angle with respect to an insertion direction of the linear interventional device, the second ultrasound image is captured by emitting ultrasonic waves toward the target subject along a second angle with respect to the insertion direction of the linear interventional device, and the second angle is closer to 90 degrees than the first angle.

3. The method of claim 1, wherein the identifying one or more line segments in the second ultrasound image by processing the second ultrasound image using a first line detection algorithm comprises:

generating a binary image by performing a binary operation on at least a portion of the second ultrasound image;

obtaining one or more lines by processing the binary image using the Hough transform algorithm;

for each of the one or more lines, determining, in the binary image, a plurality of pixel points that correspond to the linear interventional device and are located on the line; and determining a line segment corresponding to the line based on the plurality of pixel points.

4. The method of claim 1, wherein the determining a corrected line segment by processing the target region in the second ultrasound image corresponding to the line segment using a second line detection algorithm comprises:

for each of the one or more line segments, generating a plurality of rotation images by rotating the target region;

for each of the plurality of rotation images, determining a sum of pixel values on each row of the rotation image;

determining a target row with a maximum sum among a plurality of rows in the plurality of rotation images and a rotation angle of the rotation image corresponding to the target row; and determining the corrected line segment based on the target row and the rotation angle.

5. The method of claim 4, wherein the generating a plurality of rotation images by rotating the target region comprises:

obtaining a filtered image by filtering the target region using a Gabor filtering algorithm; and generating the plurality of rotation images by rotating the filtered image.

6. The method of claim 1, wherein the generating a fused ultrasound image of the first ultrasound image and the second ultrasound image based on one or more corrected line segments corresponding to the one or more line segments comprises:

for each of the one or more corrected line segments, determining an image window corresponding to the corrected line segment from the second ultrasound image based on an angle of the corrected line segment in the second ultrasound image, the angle of the corrected line segment referring to an inclination angle of the corrected line segment in the second ultrasound image;

determining a target weight of the image window, the target weight being associated with a probability that the corrected line segment corresponds to the linear interventional device; and generating the fused ultrasound image by fusing the first ultrasound image and the image window of each corrected line segment based on the target weight.

7. The method of claim 6, wherein the determining a target weight of the image window comprises:

obtaining an initial weight of the image window;

generating a plurality of vertical lines on the corrected line segment corresponding to the image window;

determining whether pixel values of a plurality of pixel points on each of the plurality of vertical lines satisfy a first preset condition;

in response to determining that the first preset condition is satisfied, determining the target weight of the image window based on the initial weight of the image window and a preset coefficient.

8. The method of claim 6, wherein the generating the fused ultrasound image by fusing the first ultrasound image and the image window of each corrected line segment based on the target weight comprises:

for each corrected line segment, determining a sub-weight of each pixel point in the image window corresponding to the corrected line segment based on the target weight of the image window;

determining a weighted image window by processing each pixel point in the image window based on the sub-weight of each pixel point; and generating the fused ultrasound image by fusing the first ultrasound image and the weighted image window of each corrected line segment.

9. The method of claim 8, wherein the determining a sub-weight of each pixel point in the image window corresponding to the corrected line segment based on the target weight of the image window comprises:

determining the sub-weight of each pixel point in the image window corresponding to the corrected line segment by multiplying the target weight of the image window by a weight coefficient, wherein a weight coefficient corresponding to a pixel point near a center of the image window is the largest, and a weight coefficient corresponding to a pixel point near an edge of the image window is the smallest.

10. The method of claim 6, wherein the determining whether pixel values of a plurality of pixel points on each of the plurality of vertical lines satisfy a first preset condition comprises:

determining an average value of each of the plurality of vertical lines based on the pixel values of the plurality of pixel points on the vertical line;

determining multiple maximum values among the plurality of average values corresponding to the plurality of vertical lines;

generating a curve, wherein a horizontal axis of the curve represents positions of the plurality of vertical lines, a vertical axis of the curve represents the average value corresponding to each vertical line, and peaks in the curve are the multiple maximum values; and determining whether the pixel values of the plurality of pixel points on each of the plurality of vertical lines satisfy the first preset condition by determining whether the vertical lines corresponding to the maximum values are equally spaced.

11. The method of claim 1, further comprising:

obtaining a third ultrasound image of the linear interventional device captured after the first ultrasound image and the second ultrasound image;

determining whether the third ultrasound image satisfies a second preset condition, the second preset condition indicating that a displacement of the linear interventional device does not exceed a displacement threshold;

in response to determining that the third ultrasound image satisfies the second preset condition, generating a second fused image of the third ultrasound image and the second ultrasound image based on the corrected line segment corresponding to each of the one or more line segments; or in response to determining that the third ultrasound image does not satisfy the second preset condition, obtaining a fourth ultrasound image having a better imaging quality with respect to the linear interventional device than the third ultrasound image for generating the second fused image.

12. A system for ultrasound image processing, comprising:

at least one storage device including a set of instructions; and at least one processor configured to communicate with the at least one storage device, wherein when executing the set of instructions, the at least one processor is configured to direct the system to perform operations including:

obtaining a first ultrasound image and a second ultrasound image of a target subject, the first ultrasound image and the second ultrasound image including a linear interventional device within the target subject, the first ultrasound image and the second ultrasound image being captured by emitting different ultrasonic waves toward the target subject, and the second ultrasound image having a better imaging quality with respect to the linear interventional device than the first ultrasound image;

identifying one or more line segments in the second ultrasound image by processing the second ultrasound image using a first line detection algorithm, wherein the first line detection algorithm is a Hough transform algorithm;

for each of the one or more line segments, determining a target region in the second ultrasound image corresponding to the line segment, wherein the target region is a local image region in the second ultrasound image including the line segment;

determining a corrected line segment by processing the target region in the second ultrasound image corresponding to the line segment using a second line detection algorithm, wherein the second line detection algorithm is a Radon transform algorithm, and a detection precision of the second line detection algorithm is higher than a detection precision of the first line detection algorithm; and generating a fused ultrasound image of the first ultrasound image and the second ultrasound image based on one or more corrected line segments corresponding to the one or more line segments.

13. The system of claim 12, wherein the first ultrasound image is captured by emitting ultrasonic waves toward the target subject along a first angle with respect to an insertion direction of the linear interventional device, the second ultrasound image is captured by emitting ultrasonic waves toward the target subject along a second angle with respect to the insertion direction of the linear interventional device, and the second angle is closer to 90 degrees than the first angle.

14. The system of claim 12, wherein the identifying one or more line segments in the second ultrasound image by processing the second ultrasound image using a first line detection algorithm comprises:

generating a binary image by performing a binary operation on at least a portion of the second ultrasound image;

obtaining one or more lines by processing the binary image using the Hough transform algorithm;

for each of the one or more lines, determining, in the binary image, a plurality of pixel points that correspond to the linear interventional device and are located on the line; and determining a line segment corresponding to the line based on the plurality of pixel points.

15. The system of claim 12, wherein the determining a corrected line segment by processing the target region in the second ultrasound image corresponding to the line segment using a second line detection algorithm comprises:

for each of the one or more line segments, generating a plurality of rotation images by rotating the target region;

for each of the plurality of rotation images, determining a sum of pixel values on each row of the rotation image;

determining a target row with a maximum sum among a plurality of rows in the plurality of rotation images and a rotation angle of the rotation image corresponding to the target row; and determining the corrected line segment based on the target row and the rotation angle.

16. The system of claim 12, wherein the generating a fused ultrasound image of the first ultrasound image and the second ultrasound image based on one or more corrected line segments corresponding to the one or more line segments comprises:

for each of the one or more corrected line segments, determining an image window corresponding to the corrected line segment from the second ultrasound image based on an angle of the corrected line segment in the second ultrasound image, the angle of the corrected line segment referring to an inclination angle of the corrected line segment in the second ultrasound image;

determining a target weight of the image window, the target weight being associated with a probability that the corrected line segment corresponds to the linear interventional device; and generating the fused ultrasound image by fusing the first ultrasound image and the image window of each corrected line segment based on the target weight.

17. The system of claim 16, wherein the determining a target weight of the image window comprises:

obtaining an initial weight of the image window;

generating a plurality of vertical lines on the corrected line segment corresponding to the image window;

determining whether pixel values of a plurality of pixel points on each of the plurality of vertical lines satisfy a first preset condition;

in response to determining that the first preset condition is satisfied, determining the target weight of the image window based on the initial weight of the image window and a preset coefficient.

18. The system of claim 16, wherein the generating the fused ultrasound image by fusing the first ultrasound image and the image window of each corrected line segment based on the target weight comprises:

for each corrected line segment, determining a sub-weight of each pixel point in the image window corresponding to the corrected line segment based on the target weight of the image window;

determining a weighted image window by processing each pixel point in the image window based on the sub-weight of each pixel point; and generating the fused ultrasound image by fusing the first ultrasound image and the weighted image window of each corrected line segment.

19. The system of claim 12, the operations further comprise:

obtaining a third ultrasound image of the linear interventional device captured after the first ultrasound image and the second ultrasound image;

determining whether the third ultrasound image satisfies a second preset condition, the second preset condition indicating that a displacement of the linear interventional device does not exceed a displacement threshold;

in response to determining that the third ultrasound image satisfies the second preset condition, generating a second fused image of the third ultrasound image and the second ultrasound image based on the corrected line segment corresponding to each of the one or more line segments; or in response to determining that the third ultrasound image does not satisfy the second preset condition, obtaining a fourth ultrasound image having a better imaging quality with respect to the linear interventional device than the third ultrasound image for generating the second fused image.

20. A non-transitory computer readable medium, comprising executable instructions that, when executed by at least one processor, direct the at least one processor to perform a method, the method comprising:

obtaining a first ultrasound image and a second ultrasound image of a target subject, the first ultrasound image and the second ultrasound image including a linear interventional device within the target subject, the first ultrasound image and the second ultrasound image being captured by emitting different ultrasonic waves toward the target subject, and the second ultrasound image having a better imaging quality with respect to the linear interventional device than the first ultrasound image;

identifying one or more line segments in the second ultrasound image by processing the second ultrasound image using a first line detection algorithm, wherein the first line detection algorithm is a Hough transform algorithm;

for each of the one or more line segments, determining a target region in the second ultrasound image corresponding to the line segment, wherein the target region is a local image region in the second ultrasound image including the line segment;

determining a corrected line segment by processing the target region in the second ultrasound image corresponding to the line segment using a second line detection algorithm, wherein the second line detection algorithm is a Radon transform algorithm, and a detection precision of the second line detection algorithm is higher than a detection precision of the first line detection algorithm; and generating a fused ultrasound image of the first ultrasound image and the second ultrasound image based on one or more corrected line segments corresponding to the one or more line segments, including:

for each of the one or more corrected line segments, determining an image window corresponding to the corrected line segment from the second ultrasound image based on an angle of the corrected line segment in the second ultrasound image;

determining a target weight of the image window, the target weight being associated with a probability that the corrected line segment corresponds to the linear interventional device; and generating the fused ultrasound image by fusing the first ultrasound image and the image window of each corrected line segment based on the target weight.

* * * * *